US008409206B2

(12) United States Patent
Wallace et al.

(10) Patent No.: US 8,409,206 B2
(45) Date of Patent: *Apr. 2, 2013

(54) TISSUE MODIFICATION DEVICES AND METHODS

(75) Inventors: Michael P. Wallace, Pleasanton, CA (US); Robert Garabedian, Mountain View, CA (US); Nestor C. Cantorna, Fremont, CA (US); Jeffery L. Bleich, Palo Alto, CA (US); Roy Leguidleguid, Union City, CA (US); Ronald Leguidleguid, Fremont, CA (US)

(73) Assignee: Baxano, Inc., San Jose, CA (US)

( * ) Notice: Subject to any disclaimer, the term of this patent is extended or adjusted under 35 U.S.C. 154(b) by 365 days.

This patent is subject to a terminal disclaimer.

(21) Appl. No.: 12/773,595

(22) Filed: May 4, 2010

(65) Prior Publication Data

US 2010/0274250 A1 Oct. 28, 2010

Related U.S. Application Data

(63) Continuation-in-part of application No. 12/496,094, filed on Jul. 1, 2009, which is a continuation-in-part of application No. PCT/US2009/050492, filed on Jul. 14, 2009.

(60) Provisional application No. 61/175,323, filed on May 4, 2009, provisional application No. 61/254,638, filed on Oct. 23, 2009, provisional application No. 61/285,188, filed on Dec. 10, 2009, provisional application No. 61/077,441, filed on Jul. 1, 2008, provisional application No. 61/080,647, filed on Jul. 14, 2008, provisional application No. 61/081,685, filed on Jul. 17, 2008, provisional application No. 61/163,699, filed on Mar. 26, 2009.

(51) Int. Cl.
*A61B 17/00* (2006.01)

(52) U.S. Cl. .......................................................... 606/79
(58) Field of Classification Search .................. 606/79, 606/82, 84, 85, 176, 177
See application file for complete search history.

(56) References Cited

U.S. PATENT DOCUMENTS

| 184,804 A | 11/1876 | Stohlmann |
| 289,104 A | 11/1883 | How |

(Continued)

FOREIGN PATENT DOCUMENTS

| DE | 3209403 A1 | 9/1983 |
| DE | 4036804 A1 | 5/1992 |

(Continued)

OTHER PUBLICATIONS

Arcenio et al.; U.S. Appl. No. 12/980,165 entitled "Systems and Methods for Performing Spinal Fusion", filed Dec. 28, 2010.

(Continued)

*Primary Examiner* — Nicholas Woodall
(74) *Attorney, Agent, or Firm* — Shay Glenn LLP

(57) ABSTRACT

Described herein are devices, systems and methods for cutting tissue in a patient. In some embodiments, a tissue modification region of a device includes a pair of flexible elongate cutting members extending along the length of the tissue modification region. Each elongate cutting member may be configured to cut a discrete trough into tissue to a depth that is greater than the thickness of the cutting member. In some embodiments, the device includes a spacer. The spacer may be sized and configured to operate in one of two modes. A first mode, in which the spacer is coupled to the cutting members such that it holds a portion of each of the two cutting members a distance from one another, and a second mode, in which at least a portion of the spacer is moved away from a cutting member to allow the cutting members to cut further into tissue.

19 Claims, 23 Drawing Sheets

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman et al. |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashef |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |

| | | | | | | |
|---|---|---|---|---|---|---|
| 5,697,889 | A | 12/1997 | Slotman et al. | 6,236,892 B1 | 5/2001 | Feler |
| 5,709,697 | A | 1/1998 | Ratcliff et al. | 6,251,115 B1 | 6/2001 | Williams et al. |
| 5,725,530 | A | 3/1998 | Popken | 6,256,540 B1 | 7/2001 | Panescu et al. |
| 5,735,792 | A | 4/1998 | Vanden Hoek et al. | 6,259,945 B1 | 7/2001 | Epstein et al. |
| 5,755,732 | A | 5/1998 | Green et al. | 6,261,582 B1 | 7/2001 | Needham et al. |
| 5,759,159 | A | 6/1998 | Masreliez | 6,266,551 B1 | 7/2001 | Osadchy et al. |
| 5,762,629 | A | 6/1998 | Kambin | 6,266,558 B1 | 7/2001 | Gozani et al. |
| 5,766,168 | A | 6/1998 | Mantell | 6,267,760 B1 | 7/2001 | Swanson |
| 5,769,865 | A | 6/1998 | Kermode et al. | 6,272,367 B1 | 8/2001 | Chance |
| 5,775,331 | A | 7/1998 | Raymond et al. | 6,277,094 B1 | 8/2001 | Schendel |
| 5,779,642 | A | 7/1998 | Nightengale | 6,280,447 B1 | 8/2001 | Marino et al. |
| 5,788,653 | A | 8/1998 | Lorenzo | 6,292,702 B1 | 9/2001 | King et al. |
| 5,792,044 | A | 8/1998 | Foley et al. | 6,298,256 B1 | 10/2001 | Meyer |
| 5,795,308 | A | 8/1998 | Russin | 6,312,392 B1 | 11/2001 | Herzon |
| 5,800,350 | A | 9/1998 | Coppleson et al. | 6,324,418 B1 | 11/2001 | Crowley et al. |
| 5,803,902 | A | 9/1998 | Sienkiewicz et al. | 6,324,432 B1 | 11/2001 | Rigaux et al. |
| 5,803,904 | A | 9/1998 | Mehdizadeh | 6,325,764 B1 | 12/2001 | Griffith et al. |
| 5,807,263 | A | 9/1998 | Chance | 6,334,068 B1 | 12/2001 | Hacker |
| 5,810,744 | A | 9/1998 | Chu et al. | 6,343,226 B1 | 1/2002 | Sunde et al. |
| 5,813,405 | A | 9/1998 | Montano, Jr. et al. | 6,358,254 B1 | 3/2002 | Anderson |
| 5,824,040 | A | 10/1998 | Cox et al. | 6,360,750 B1 | 3/2002 | Gerber et al. |
| 5,830,151 | A | 11/1998 | Hadzic et al. | 6,364,886 B1 | 4/2002 | Sklar |
| 5,830,157 | A | 11/1998 | Foote | 6,368,324 B1 | 4/2002 | Dinger et al. |
| 5,830,188 | A | 11/1998 | Abouleish | 6,370,411 B1 | 4/2002 | Osadchy et al. |
| 5,833,692 | A | 11/1998 | Cesarini et al. | 6,370,435 B2 | 4/2002 | Panescu et al. |
| 5,836,810 | A | 11/1998 | Åsum | 6,383,509 B1 | 5/2002 | Donovan et al. |
| 5,836,948 | A | 11/1998 | Zucherman et al. | 6,390,906 B1 | 5/2002 | Subramanian |
| 5,843,110 | A | 12/1998 | Dross et al. | 6,391,028 B1 | 5/2002 | Fanton et al. |
| 5,846,196 | A | 12/1998 | Siekmeyer et al. | 6,416,505 B1 | 7/2002 | Fleischman et al. |
| 5,846,244 | A | 12/1998 | Cripe | 6,423,071 B1 | 7/2002 | Lawson |
| 5,851,191 | A | 12/1998 | Gozani | 6,423,080 B1 | 7/2002 | Gellman et al. |
| 5,851,209 | A | 12/1998 | Kummer et al. | 6,425,859 B1 | 7/2002 | Foley et al. |
| 5,851,214 | A | 12/1998 | Larsen et al. | 6,425,887 B1 | 7/2002 | McGuckin et al. |
| 5,853,373 | A | 12/1998 | Griffith et al. | 6,428,486 B2 | 8/2002 | Ritchart et al. |
| 5,865,844 | A | 2/1999 | Plaia et al. | 6,436,101 B1 | 8/2002 | Hamada |
| 5,868,767 | A | 2/1999 | Farley et al. | 6,442,848 B1 | 9/2002 | Dean |
| 5,879,353 | A | 3/1999 | Terry | 6,446,621 B1 | 9/2002 | Svensson |
| 5,885,219 | A | 3/1999 | Nightengale | 6,451,335 B1 | 9/2002 | Goldenheim et al. |
| 5,895,417 | A | 4/1999 | Pomeranz et al. | 6,454,767 B2 | 9/2002 | Alleyne |
| 5,897,583 | A | 4/1999 | Meyer et al. | 6,464,682 B1 | 10/2002 | Snoke |
| 5,899,909 | A | 5/1999 | Claren et al. | 6,466,817 B1 | 10/2002 | Kaula et al. |
| 5,904,657 | A | 5/1999 | Unsworth et al. | 6,468,289 B1 | 10/2002 | Bonutti |
| 5,916,173 | A | 6/1999 | Kirsner | 6,470,209 B2 | 10/2002 | Snoke |
| 5,918,604 | A | 7/1999 | Whelan | 6,478,805 B1 | 11/2002 | Marino et al. |
| 5,919,190 | A | 7/1999 | VanDusseldorp | 6,487,439 B1 | 11/2002 | Skladnev et al. |
| 5,928,158 | A | 7/1999 | Aristides | 6,488,636 B2 | 12/2002 | Bryan et al. |
| 5,928,159 | A | 7/1999 | Eggers et al. | 6,491,646 B1 | 12/2002 | Blackledge |
| 5,941,822 | A | 8/1999 | Skladnev et al. | 6,500,128 B2 | 12/2002 | Marino |
| 5,961,522 | A | 10/1999 | Mehdizadeh | 6,500,189 B1 | 12/2002 | Lang et al. |
| 5,972,013 | A | 10/1999 | Schmidt | 6,512,958 B1 | 1/2003 | Swoyer et al. |
| 5,976,110 | A | 11/1999 | Greengrass et al. | 6,516,223 B2 | 2/2003 | Hofmann |
| 5,976,146 | A | 11/1999 | Ogawa et al. | 6,520,907 B1 | 2/2003 | Foley et al. |
| 6,002,964 | A | 12/1999 | Feler et al. | 6,527,786 B1 | 3/2003 | Davis et al. |
| 6,004,326 | A | 12/1999 | Castro et al. | 6,533,749 B1 | 3/2003 | Mitusina et al. |
| 6,004,330 | A | 12/1999 | Middleman et al. | 6,535,759 B1 | 3/2003 | Epstein et al. |
| 6,010,493 | A | 1/2000 | Snoke | 6,540,742 B1 | 4/2003 | Thomas et al. |
| 6,015,406 | A | 1/2000 | Goble et al. | 6,540,761 B2 | 4/2003 | Houser |
| 6,022,362 | A | 2/2000 | Lee et al. | 6,546,270 B1 | 4/2003 | Goldin et al. |
| 6,030,383 | A | 2/2000 | Benderev | 6,558,353 B2 | 5/2003 | Zohmann |
| 6,030,401 | A | 2/2000 | Marino | 6,558,390 B2 | 5/2003 | Cragg |
| 6,038,480 | A | 3/2000 | Hrdlicka et al. | 6,562,033 B2 | 5/2003 | Shah et al. |
| 6,048,345 | A | 4/2000 | Berke et al. | 6,564,078 B1 | 5/2003 | Marino et al. |
| 6,068,642 | A | 5/2000 | Johnson et al. | 6,564,079 B1 | 5/2003 | Cory et al. |
| 6,073,051 | A | 6/2000 | Sharkey et al. | 6,564,088 B1 | 5/2003 | Soller et al. |
| 6,099,514 | A | 8/2000 | Sharkey et al. | 6,569,160 B1 | 5/2003 | Goldin et al. |
| 6,102,930 | A | 8/2000 | Simmons, Jr. | 6,575,979 B1 | 6/2003 | Cragg |
| 6,106,558 | A | 8/2000 | Picha | 6,579,291 B1 | 6/2003 | Keith et al. |
| 6,113,534 | A | 9/2000 | Koros et al. | 6,584,345 B2 | 6/2003 | Govari |
| D432,384 | S | 10/2000 | Simons | 6,592,559 B1 | 7/2003 | Pakter et al. |
| 6,132,387 | A | 10/2000 | Gozani et al. | 6,595,932 B2 | 7/2003 | Ferrera |
| 6,136,014 | A | 10/2000 | Sirimanne et al. | 6,597,955 B2 | 7/2003 | Panescu et al. |
| 6,142,993 | A | 11/2000 | Whayne et al. | 6,606,523 B1 | 8/2003 | Jenkins |
| 6,142,994 | A | 11/2000 | Swanson et al. | 6,607,530 B1 | 8/2003 | Carl et al. |
| 6,146,380 | A | 11/2000 | Racz et al. | 6,609,018 B2 | 8/2003 | Cory et al. |
| 6,152,894 | A | 11/2000 | Kubler | 6,610,066 B2 | 8/2003 | Dinger et al. |
| 6,169,916 | B1 | 1/2001 | West | 6,620,129 B2 | 9/2003 | Stecker et al. |
| 6,205,360 | B1 | 3/2001 | Carter et al. | 6,622,731 B2 | 9/2003 | Daniel et al. |
| 6,214,001 | B1 | 4/2001 | Casscells et al. | 6,624,510 B1 | 9/2003 | Chan et al. |
| 6,214,016 | B1 | 4/2001 | Williams et al. | 6,626,916 B1 | 9/2003 | Yeung et al. |

| | | |
|---|---|---|
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,699,246 B2 | 3/2004 | Zucherman et al. |
| 6,723,049 B2 | 4/2004 | Blunsden et al. |
| 6,726,531 B1 | 4/2004 | Harrel |
| 6,726,685 B2 | 4/2004 | To et al. |
| 6,733,496 B2 | 5/2004 | Ashley et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Pintauro et al. |
| 6,760,616 B2 | 7/2004 | Hoey et al. |
| 6,764,491 B2 | 7/2004 | Frey et al. |
| 6,772,012 B2 | 8/2004 | Woloszko et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Cragg et al. |
| 6,795,737 B2 | 9/2004 | Gielen et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,172,562 B2 | 2/2007 | McKinley |
| 7,177,677 B2 | 2/2007 | Kaula et al. |
| 7,181,289 B2 | 2/2007 | Pflueger et al. |
| 7,189,240 B1 | 3/2007 | Dekel |
| 7,192,430 B2 | 3/2007 | Truckai et al. |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,238,189 B2 | 7/2007 | Schmieding et al. |
| 7,239,911 B2 | 7/2007 | Scholz |
| 7,245,789 B2 | 7/2007 | Bates et al. |
| 7,270,658 B2 | 9/2007 | Woloszko et al. |
| 7,270,659 B2 | 9/2007 | Ricart et al. |
| 7,282,033 B2 | 10/2007 | Urmey |
| 7,282,061 B2 | 10/2007 | Sharkey et al. |
| 7,295,881 B2 | 11/2007 | Cohen et al. |
| 7,318,823 B2 | 1/2008 | Sharps et al. |
| 7,337,005 B2 | 2/2008 | Kim et al. |
| 7,337,006 B2 | 2/2008 | Kim et al. |
| 7,367,972 B2 | 5/2008 | Francischelli et al. |
| 7,383,639 B2 | 6/2008 | Malandain |
| 7,390,330 B2 | 6/2008 | Harp |
| 7,419,487 B2 | 9/2008 | Johnson et al. |
| 7,449,019 B2 | 11/2008 | Uchida et al. |
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eggers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Kaula et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |

| | | |
|---|---|---|
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0030330 A1 | 2/2004 | Brassell et al. |
| 2004/0049208 A1 | 3/2004 | Hill et al. |
| 2004/0064058 A1 | 4/2004 | McKay |
| 2004/0097927 A1 | 5/2004 | Yeung et al. |
| 2004/0098074 A1 | 5/2004 | Erickson et al. |
| 2004/0106940 A1 | 6/2004 | Shaolian et al. |
| 2004/0111084 A1 | 6/2004 | Brett |
| 2004/0122433 A1 | 6/2004 | Loubens et al. |
| 2004/0122482 A1 | 6/2004 | Tung et al. |
| 2004/0127893 A1 | 7/2004 | Hovda |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0225233 A1 | 11/2004 | Frankowski et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0149035 A1 | 7/2005 | Pimenta et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089633 A1 | 4/2006 | L. Bleich et al. |
| 2006/0089640 A1 | 4/2006 | Bleich et al. |
| 2006/0089650 A1 | 4/2006 | Nolde |
| 2006/0089688 A1 | 4/2006 | Panescu |
| 2006/0094976 A1 | 5/2006 | Bleich |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0086114 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0197024 A1 | 8/2008 | Simpson et al. |
| 2008/0200912 A1 | 8/2008 | Long |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |

| | | | |
|---|---|---|---|
| 2009/0018507 A1 | 1/2009 | Schmitz et al. | |
| 2009/0018610 A1 | 1/2009 | Gharib et al. | |
| 2009/0054804 A1 | 2/2009 | Gharib et al. | |
| 2009/0054936 A1 | 2/2009 | Eggen et al. | |
| 2009/0054941 A1 | 2/2009 | Eggen et al. | |
| 2009/0062871 A1 | 3/2009 | Chin et al. | |
| 2009/0062872 A1 | 3/2009 | Chin et al. | |
| 2009/0069709 A1 | 3/2009 | Schmitz et al. | |
| 2009/0082763 A1 | 3/2009 | Quick et al. | |
| 2009/0105604 A1 | 4/2009 | Bertagnoli et al. | |
| 2009/0105788 A1 | 4/2009 | Bartol et al. | |
| 2009/0118709 A1 | 5/2009 | Sand et al. | |
| 2009/0124934 A1 | 5/2009 | Rabbitte et al. | |
| 2009/0125036 A1 | 5/2009 | Bleich | |
| 2009/0138056 A1 | 5/2009 | Anderson et al. | |
| 2009/0143807 A1 | 6/2009 | Sand | |
| 2009/0143829 A1 | 6/2009 | Shluzas | |
| 2009/0149865 A1 | 6/2009 | Schmitz et al. | |
| 2009/0171381 A1 | 7/2009 | Schmitz et al. | |
| 2009/0177112 A1 | 7/2009 | Gharib et al. | |
| 2009/0177144 A1 | 7/2009 | Masmanidis et al. | |
| 2009/0177241 A1 | 7/2009 | Bleich et al. | |
| 2009/0182382 A1 | 7/2009 | Justis et al. | |
| 2009/0204119 A1 | 8/2009 | Bleich et al. | |
| 2009/0209879 A1 | 8/2009 | Kaula et al. | |
| 2009/0216284 A1 | 8/2009 | Chin et al. | |
| 2009/0299166 A1 | 12/2009 | Nishida et al. | |
| 2010/0004654 A1 | 1/2010 | Schmitz et al. | |
| 2010/0010334 A1 | 1/2010 | Bleich et al. | |
| 2010/0057087 A1 | 3/2010 | Cha | |
| 2010/0094231 A1 | 4/2010 | Bleich et al. | |
| 2010/0331883 A1 | 12/2010 | Schmitz et al. | |
| 2010/0331900 A1 | 12/2010 | Garabedian et al. | |
| 2011/0004207 A1 | 1/2011 | Wallace et al. | |
| 2011/0046613 A1 | 2/2011 | Schmitz et al. | |
| 2011/0060314 A1 | 3/2011 | Wallace et al. | |
| 2011/0112539 A1 | 5/2011 | Wallace et al. | |
| 2011/0160731 A1 | 6/2011 | Bleich et al. | |
| 2011/0160772 A1 | 6/2011 | Arcenio et al. | |
| 2011/0190772 A1 | 8/2011 | Saadat et al. | |
| 2011/0196257 A1 | 8/2011 | Schmitz et al. | |
| 2011/0224709 A1 | 9/2011 | Bleich | |
| 2011/0224710 A1 | 9/2011 | Bleich | |
| 2012/0016368 A1 | 1/2012 | Bleich et al. | |
| 2012/0022538 A1 | 1/2012 | Schmitz et al. | |
| 2012/0065639 A1 | 3/2012 | Schmitz et al. | |
| 2012/0078255 A1 | 3/2012 | Bleich et al. | |
| 2012/0095468 A1 | 4/2012 | Wallace et al. | |
| 2012/0123294 A1 | 5/2012 | Sun et al. | |
| 2012/0143206 A1 | 6/2012 | Wallace et al. | |

FOREIGN PATENT DOCUMENTS

| | | | |
|---|---|---|---|
| EP | 359883 A1 | 3/1990 | |
| EP | 1304080 A2 | 4/2003 | |
| EP | 1340467 A2 | 9/2003 | |
| EP | 1207794 B1 | 5/2004 | |
| EP | 1315463 B1 | 5/2005 | |
| EP | 1611851 A1 | 1/2006 | |
| EP | 1006885 B1 | 9/2006 | |
| FR | 2706309 | 12/1994 | |
| JP | 2960140 B2 | 10/1999 | |
| JP | 23116868 | 4/2003 | |
| JP | 24065380 A2 | 3/2004 | |
| RU | 2107459 | 3/1998 | |
| WO | WO 92/22259 A2 | 12/1992 | |
| WO | WO-96/22057 | 7/1996 | |
| WO | WO 97/14362 A1 | 4/1997 | |
| WO | WO-97/34536 A2 | 9/1997 | |
| WO | WO-99/18866 A1 | 4/1999 | |
| WO | WO-99/21500 A1 | 5/1999 | |
| WO | WO-00/67651 A1 | 11/2000 | |
| WO | WO-01/08571 A1 | 2/2001 | |
| WO | WO-01/62168 A2 | 8/2001 | |
| WO | WO-02/07901 A1 | 1/2002 | |
| WO | WO-02/34120 A2 | 5/2002 | |
| WO | WO-02/076311 A2 | 10/2002 | |
| WO | WO-03/026482 A2 | 4/2003 | |
| WO | WO-03/066147 A1 | 8/2003 | |
| WO | WO-2004/002331 A1 | 1/2004 | |
| WO | WO-2004/028351 A2 | 4/2004 | |
| WO | WO-20041043272 A1 | 5/2004 | |
| WO | WO-2004/056267 A1 | 7/2004 | |
| WO | WO-2004/078066 A2 | 9/2004 | |
| WO | WO-2004/080316 A1 | 9/2004 | |
| WO | WO-2004/096080 A2 | 11/2004 | |
| WO | WO-2005/009300 A1 | 2/2005 | |
| WO | WO-2005/057467 A2 | 6/2005 | |
| WO | WO-2005/077282 A1 | 8/2005 | |
| WO | WO-2005/089433 A2 | 9/2005 | |
| WO | WO-2006/009705 A2 | 1/2006 | |
| WO | WO-2006/015302 A1 | 2/2006 | |
| WO | WO-2006/017507 A2 | 2/2006 | |
| WO | WO-2006/039279 A2 | 4/2006 | |
| WO | WO-2006/042206 A2 | 4/2006 | |
| WO | WO-2006/044727 A2 | 4/2006 | |
| WO | WO-2006/047598 A1 | 5/2006 | |
| WO | WO-2006/058079 A3 | 6/2006 | |
| WO | WO-2006/058195 A2 | 6/2006 | |
| WO | WO-2006/062555 A2 | 6/2006 | |
| WO | WO-2006/086241 A2 | 8/2006 | |
| WO | WO-2006/099285 A2 | 9/2006 | |
| WO | WO-2006/102085 A2 | 9/2006 | |
| WO | WO-2007/008709 A2 | 1/2007 | |
| WO | WO-2007/021588 A1 | 2/2007 | |
| WO | WO-2007/022194 A2 | 2/2007 | |
| WO | WO-20071059343 A2 | 2/2007 | |
| WO | WO-2007/067632 A2 | 6/2007 | |
| WO | WO-2008/008898 A2 | 1/2008 | |
| WO | WO-2008/157513 A1 | 12/2008 | |
| WO | WO-2009/012265 A2 | 1/2009 | |
| WO | WO-2009/018220 A1 | 2/2009 | |
| WO | WO-20091021116 A2 | 2/2009 | |
| WO | WO-2009/036156 A1 | 3/2009 | |
| WO | WO-2009/046046 A1 | 4/2009 | |
| WO | WO-2009/058566 A1 | 5/2009 | |
| WO | WO-2009/151926 A2 | 12/2009 | |
| WO | WO-2010/014538 | 4/2010 | |

OTHER PUBLICATIONS

Bleich et al.; U.S. Appl. No. 12/984,162 entitled "Devices and Methods for Tissue Access", filed Jan. 4, 2011.

Schmitz et al.; U. S. Appl. No. 12/917,253; entitled "Tissue Access Guidewire System and Method"; filed Nov. 1, 2010.

Wallace et al.; U.S. Appl. No. 12/911,537 entitled "Devices and Methods for Treating Tissue", filed Oct. 25, 2010.

Wallace et al.; U.S. Appl. No. 13/007,381 entitled "Tissue Modification Devices", filed Jan. 14, 2011.

Bleich et al.; U.S. Appl. No. 13/484,744 entitled "Devices and Methods for Tissue Modification," filed May 31, 2012.

Bleich et al.; U.S. Appl. No. 13/430,500 entitled "Devices and Methods for Tissue Modification," filed Mar. 26, 2012.

Garabedian et al.; U.S. Appl. No. 13/437,214 entitled "Flexible Tissue Rasp," filed Apr. 2, 2012.

US Surgical Kerrison Spinal Rongeur K943116 [online] Retrieved from the Internet: <URL: http://www.ussurg.com/uss/index.html>. Jul. 27, 1994.

Zeppelin Laminectomy Rongeur K901372, [online] Retrieved from the Internet: <URL: http://www.zeppelin-medical.com/download/instruments.pdf>. Oct. 24, 2006.

Ellman Int. Disc-FX System Accessories K052241 [online] Retrieved from the Internet: <URL: http://www.ellman.com/ medical/ >. Feb. 27, 2006.

Ohta et al., "Superimposed Mechanomygraphic Response at Different Contraction Intensity in Medial Gastrocnemius and Soleus Muscles," International Journal of Sport and Health Science: vol. 5, 63-70, 2007. 2007.

Schwieger et al., "Abrasive Water Jet Cutting as a New Procedure for Cutting Cancellous Bone—in Vitro Testing in Comparison with the Oscillating Saw," Wiley Interscience, wvvw.interscience,wiley.com, Sep. 20, 2004, 223-228.Sep. 20, 2004.

Mopec Bone-Cutting tool, Product brochure, Total pp. 4. First accessed Dec. 15, 2005.

Codman Laminectomy Shaver (a Johnson & Johnson company www.codman.com) catalogue, pp. 416-431, [online] Retrieved from the Internet: <URL: http:llwww.codman.com/PDFs/Catalog_04_R.pdf>. First accessedOct. 24, 2006.
Integra Ruggles TM Kerrison Rongeurs [online] Retrieved from the internet: <URL: http://www.integra-ls.com/products!? product=22>. First accessed Oct. 24, 2006.
Herkowitz, "The Cervical Spine Surgery Atlas", Herkowitz, "The Cervical.Spine Surgery Atlas", 2004, 2nd Edition Jan. 1, 2004, 203-206, 208.
Abdel-Wanis et al., "Tumor growth potential after tumoral and instrumental contamination: an in-vivo comparative study of T-saw, Gigli saw, and scalpel," Journal of orthopaedic science, 2001, vol. 6, 424-429. Jan. 1, 2001.
Barer Malvin, "Instrument to Enhance Passage of the Gigli Saw," Journal of Pediatric Orthopedics, Raven Press, New York, 1984, 4:762-763. Jan. 1, 1984.
Baumgart et al., "Indikation and Technik der Knochendurchtrennung," Der Chirurg, 1998, vol. 69:1188-1196. (in German with Eng Summary). Jan. 1, 1998.
Bohinski et al., "Novel use of a threadwire saw for high sacral amputation," Journal of neurosurgery: Spine, 2005, vol. 3, 71-78. Jan. 1, 2005.
Brunori et al., "Celebrating the centennial (1894-1994): Leonardo Gigli and his wire saw," J. Neurosurg, 1995, 82:1086-1090. Jan. 1, 1995.
Burrows, Harold, "Surgical instruments and appliances used in operations," Faber and Faber, London, 1937, total pp. 4. Jan. 1, 1937.
Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>. Jan. 1, 2001.
Dammann, Gordon, Pictorial Encyclopedia of Civil War Medical Instruments and Equipment, Pictorial Histories Publishing Company, Missoula, Montana, 1983, Total pp. 2. Jan. 1, 1983.
Edwards et al; "T-Saw Laminoplasty for the Management of Cervical Spondylotic Myelopathy," Spine, Lippincott Williams & Wilkins, Inc., 2000, vol. 25 (14): 1788-1794. Jan. 1, 2000.
Ellman Int. Disc-FX System Accessories K052241 [online] Retrieved from the Internet: <URL: http://www.ellman.com/ medical/ >. Jan. 1, 2001.
Eralp et al., "A comparison of two osteotomy techniques for tibial lengthening," Archives of orthopaedic and trauma surgery, 2004, vol. 124:298-300. Jan. 1, 2004.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_ste Jan. 1, 2006.
Fujita et al., "Chordoma in the Cervical Spine Managed with En Bloc Excision," Spine, Lippincott Williams & Wilkins, Inc., 1999, 24 (17), 1848-1851. Jan. 1, 1999.
Garabedian et al.; U.S. Appl. No. 12/824,043; entitled "Surgical Tools for Treatment of Spinal Stenosis"; filed Jun. 25, 2010.
Goel, Atul, "Neurosurgical forum, Supraorbital Craniotomy," Journal of Neurosurgery, 1994, vol. 81, 642-643. Jan. 1, 1994.
Gore Smoother User Manual, W. L. Gore & Associates, Inc. Flagstaff, AZ, Dec. 1999,Total pp. 3. Jan. 1, 1999.
Hara et al., "En Bloc Laminoplasty Performed with Threadwire Saw: Technical Note," Neurosurgery, Jan. 2001, vol. 48, No. 1, pp. 235-239. Jan. 1, 2001.
Hata et al; "A less invasive surgery for rotator cuff tear: Mini-open repair," Journal of Shoulder and Elbow Surgery, 2001, vol. 10 No. 1, 11-16. Jan. 1, 2001.
Honl et al; "The Use of Water-Jetting Technology in Prostheses Revision Surgery—First Results of Parameter Studies on Bone and Bone Cement," J. Biomed Mater Res (Applied Biomaterials), John Wiley & Sons, Inc, 2000, 53, 6: 781-790. Jan. 1, 2000.
Integra Ruggles TM Kerrison Rongeurs [online] Retrieved from the internet: <URL: http://www.integra-ls.com/products!? product=22>. Jan. 1, 2001.
Jun, Byung-Yoon, "Posterior Lumbar Interbody Fusion With Restoration of Lamina and Facet Fusion," Spine, Lippincott Williams & Wilkins, Inc., 2000, vol. 25 No. 8, 917-922. Jan. 1, 2000.

Kawahara et al., "Recapping T-Saw Laminoplasty for Spinal Cord Tumors," Spine, 1999, vol. 24 No. 13, pp. 1363-1370. Jan. 1, 1999.
Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680-684. Jan. 1, 2003.
Miyamoto et al., "Kyphectomy Using a Surgical Threadwire (T-saw) for Kyphotic Deformity in a Child With Myelomeningocele," Spine, Lippincott Williams & Wilkins, Inc., 2003, vol. 28 No. 10, E187-E190. Jan. 1, 2003.
Mopec Bone-Cutting tool, Product brochure, Total pp. 4. Jan. 1, 2001.
Nakagiri et al., "Thoracoscopic Rib Resection Using a Gigli Saw," The Annals of Thoracic Surgery, 2005, vol. 80, 755-756. Jan. 1, 2005.
Osaka et al., "Clinical significance of a wide excision policy for sacrococcygeal chordoma," J Cancer Res Clin Oncol, 2005, Total pp. 6. Jan. 1, 2005.
Paktiss et al., "Afghan Percutaneous Osteotomy," Journal of Pediatric Orthopaedics, Raven Press Ltd, New York, 1993, vol. 13 No. 4, 531-533. Jan. 1, 1993.
Paley et al., "Percutaneous Osteotomies," Orthopedic Clinics of North America, 1991, vol. 22 No. 4, 613-624. Jan. 1, 1991.
Pancoast, Joseph, "A Treatise on Operative Surgery," Carey and Hart, Philadelphia,1844, Total pp. 11. Jan. 1, 1844.
Park et al; "Cases of the Excision of Carious Joints," John Scrymgeour, Glasgow, 1806, Total pp. 6. Jan. 1, 1806.
Peavy et al., "Comparison of Cortical Bone Ablations by Using Infrared Laser Wavelengths 2.9 to 9.2 µm, Lasers in Surgery and Medicine," 1999, vol. 26, 421-434. Jan. 1, 1999.
Peltier, Leonard Orthopedics: A History and Iconography, Norman Publishing, San Francisco, 1993, Total pp. 3. Jan. 1, 1993.
Reckling Frederick, "Modified Stethoscope Earpiece Makes Excellent Gigli Saw Guide," J Bone and Joint Surgery Am, Dec. 1972, 54-A(8), 1787-1788. Dec. 1, 1972.
Rutkow, Ira, "Surgery an Illustrated History," Mosby—Year Book, Inc., St. Louis, 1993, Total pp. 4. Jan. 1, 1993.
Schmitz et al.; U.S. Appl. No. 12/816,729 entitled Access and Tissue Modification Systems and Methods, filed Jun. 16, 2010.
Schwieger et al., "Abrasive Water Jet Cutting as a New Procedure for Cutting Cancellous Bone—In Vitro Testing in Comparison with the Oscillating Saw," Wiley Interscience, www.interscience,wiley.com, Sep. 20, 2004, 223-228. Sep. 20, 2004.
Sen, Cengiz, Tibia proksimalinde Gigli testeresi ile yapilanperkütan osteotominin guvenilirligi: Kadavra calismasi, Acta orthopaedica et traumatologica turcica, 2002, vol. 36, 136-140; (In Russian w/ Eng Summary). Jan. 1, 2002.
Shiraishi et al., "Results of Skip Laminectomy -Minimum 2-Year Follow-up Study Compared With Open-Door Laminoplasty," Spine, Lippincott Williams & Wilkins, Inc., 2003, vol. 28 No. 24, 2667-2672. Jan. 1, 2003.
Shiraishi T., "A new technique for exposure of the cervical spine laminae," Journal of neurosurgery. Spine, 2002, vol. 96(1), 122-126. Jan. 1, 2002.
Shiraishi T., Skip laminectomy—a new treatment for cervical spondylotic myelopathy, preserving bilateral muscular attachments to the spinous processes: a preliminary report, Spine, 2002, vol. 2(2), 108-115. Jan. 1, 2002.
Skippen et al., "The Chain Saw — a Scottish Invention," Scottish Medical Journal, 2004, vol. 49(2), 72-75. Jan. 1, 2004.
Stevens et al., "Calvarial Bone Graft Harvest Using the Gigli Saw," Journal of Oral and Maxillofacial Surgery, 1998, vol. 56, 798-799. Jan. 1, 1998.
Takada et al., "Unusual Metastasis to the Cauda Equina From Renal Cell Carcinoma," Spine, Lippincott Williams & Wilkins, Inc., 2003, vol. 28 No. 6, E114-E117. Jan. 1, 2003.
Tomita et al., "Expansive Midline T-Saw Laminoplasty (Modified Spinour Process-Splitting) for the Management of Cervical Myelopathy," Spine, Lippincott Williams & Wilkins, Inc, 1998, 23(1), 32-37. Jan. 1, 1998.
Tomita et al., "The Threadwire Saw: a New Device for Cutting Bone," The Journal of Bone and Joint Surgery, 1996, vol. 78, 1915-1917. Jan. 1, 1996.

Tomita et al., "The Use of the T-Saw for Expansive Midline laminoplasty in the Treatment of Cervical Myelopathy," Orthopedics and Traumatology, No. 3, pp. 169-178, 2002 Jan. 1, 2002.

Tomita et al., "Total en bloc spondylectomy and circumspinal decompression for solitary spinal metastasis," Paraplegia, 1994, 32:36-46. Jan. 1, 1994.

Tomita K. et al., "Total en bloc spondylectomy for solitary spinal metastases," International Orthopaedics (SICOT), 1994, 18: 291-298. Jan. 1, 1994.

Truax, Charles, "The Mechanics of Surgery," Chicago, IL; 1899, Total pp. 3. Jan. 1, 1899.

US Surgical Kerrison Spinal Rongeur K943116 [online] Retrieved from the internet: <URL: http://www.ussurg.com/uss/index.html>. Jan. 1, 2001.

Wallace et al.; U.S. Appl. No. 12/724,315 entitled "Flexible Neural Localization Devices and Methods," filed Mar. 15, 2010.

Wilkins, Robert H, "Neurosurgical Classics," Johnson Reprint Corporation, New York, 1965, 377-382. Jan. 1, 1965.

Zeppelin Laminectomy Rongeur K901372, [online] Retrieved from the internet: <URL: http://www.zeppelin-medical.com/download/instruments.pdf>. Jan. 1, 2001.

Schmitz et al.; U.S. Appl. No. 13/588,969 entitled "Access and Tissue Modification Systems and Methods," filed Aug. 17, 2012.

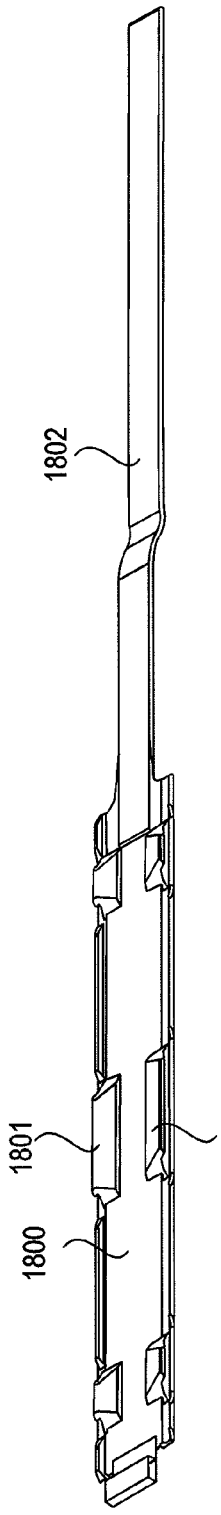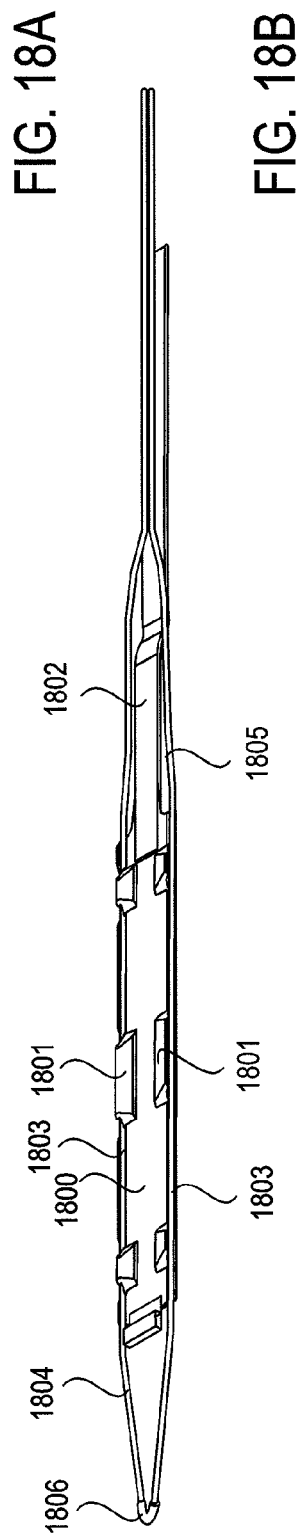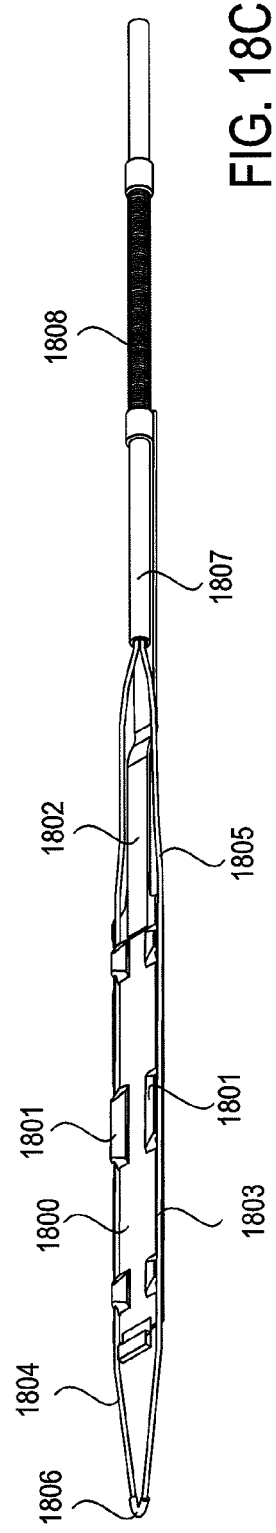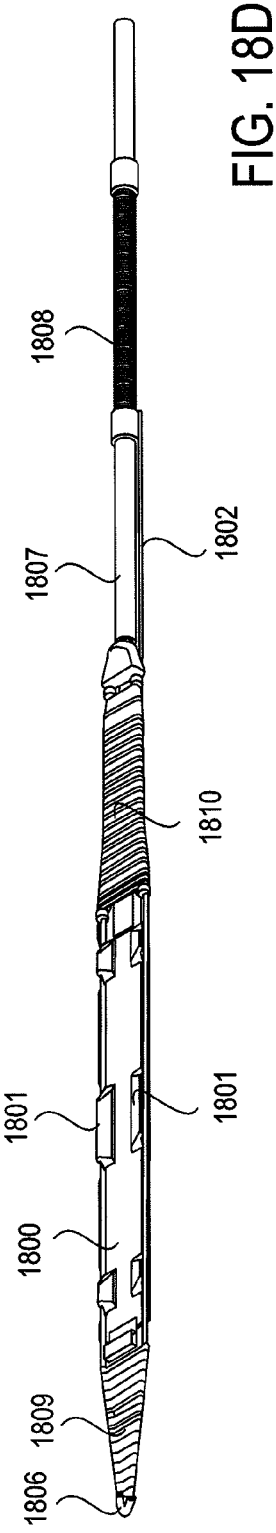

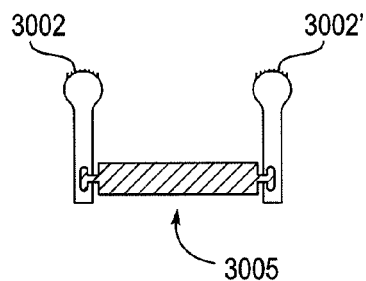 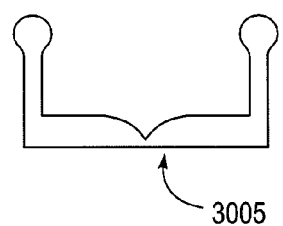
FIG. 30A  FIG. 30B
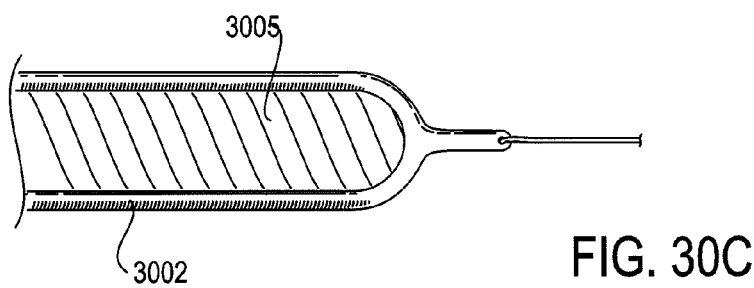
FIG. 30C
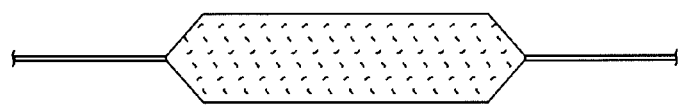
FIG. 31A
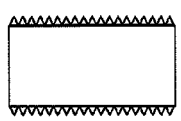 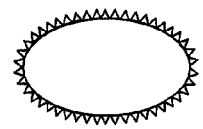 
FIG. 31B  FIG. 31C  FIG. 31D
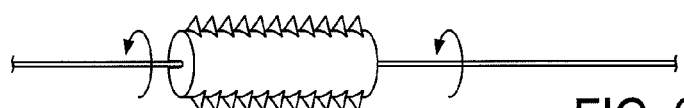
FIG. 31E

TISSUE MODIFICATION DEVICES AND METHODS

CROSS REFERENCE TO RELATED APPLICATIONS

This patent application claims priority to U.S. Provisional Application No. 61/175,323, titled "TISSUE MODIFICATION DEVICES", filed on May 4, 2009; U.S. Provisional Application No. 61/254,638, titled "SPINAL BONE CUTTING DEVICES AND METHODS", filed on Oct. 23, 2009; and U.S. Provisional Application No. 61/285,188, titled "SPINAL BONE CUTTING DEVICES AND METHODS", filed on Dec. 10, 2009.

This patent application is also a continuation-in-part to U.S. patent application Ser. No. 12/496,094, titled "ACCESS AND TISSUE MODIFICATION SYSTEMS AND METHODS", filed on Jul. 1, 2009, which claims the benefit of U.S. Provisional Application No. 61/077,441, titled "INNER SPINOUS DISTRACTION ACCESS AND DECOMPRESSION SYSTEM," filed on Jul. 1, 2008.

This patent application is also a continuation-in-part to PCT Application No. PCT/US09/50492, titled "TISSUE MODIFICATION DEVICES", filed on Jul. 14, 2009, which claims priority to U.S. Provisional Application No. 61/080,647, filed Jul. 14, 2008; U.S. Provisional Application No. 61/081,685, filed Jul. 17, 2008; and U.S. Provisional Patent Application No. 61/163,699, filed Mar. 26, 2009.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are systems, devices, and methods of using them, for cutting spinal bone and soft tissue in a way that minimizes potential damage to surrounding tissue, and particularly the spinal nerves and vasculature. The methods, devices and systems described herein may be used as part of a spinal surgical procedure involving a complete or partial removal of spinal bone or joint, such as a laminectomy, laminotomy, fascetectomy, pediculectomy, etc.

BACKGROUND OF THE INVENTION

Surgical intervention may require the manipulation of one or more medical devices in close proximity to a nerve or nerves, which may risk damage to the nerve tissue. For example, medical devices may be used to cut, extract, suture, coagulate, or otherwise manipulate tissue including tissue near or adjacent to neural tissue. Spinal decompressions, are one type of procedure that may be preformed to remove tissue that is impinging on a spinal nerve. It would be beneficial to be able to cut or manipulate tissue (and especially bone) in a way that avoids or protects nearby structures such as nerves, while allowing precise removal of bone or portions of bones.

For example, a Transforaminal Lumbar Interbody Fusion ("TLIF") procedure is a surgical technique to stabilize the spinal vertebra and the disc or shock absorber between the vertebras. In this procedure, lumbar fusion surgery creates a solid structure (bone and/or interbody device) between adjoining vertebras, eliminating any movement between the bones. The goal of the surgery is to reduce pain and nerve irritation. The procedure typically involves removal of a great deal of spinal bone, e.g., by cutting through the patients back and removing the facet joints to create an opening into which a spacer or interbody cage can be inserted and filled with bone graft material. Interbody devices such as cages or spacers are typically 8 mm wide to 15 mm wide. Pedicle screws and rods or plates may then be used to fuse the vertebra.

It is common to do a laminectomy as part of the TLIF procedure, in order to provide space for the insertion of the spacer or cage. Other, similar procedures such as Posterior Lumbar Interbody Fusion (PLIF) procedures also involve cutting and removing a region of bone from the spine, such as the removal of a portion of the inferior articulating process (IAP). Removal of these relatively large portions of bone may be difficult, and may require cutting through a substantial amount of otherwise healthy tissue. In addition, the effort of cutting through the bone may damage nearby tissue, including nerve tissue such as nerve roots which are intimately associated with the spine in the dorsal column region being modified. The risks and difficulties of the procedures described above and other such surgical procedure may be exacerbated by the need to make multiple cuts in bone and other tissues, which are typically performed sequentially.

In addition, procedures such as these that involve cutting of spinal bone must be performed in difficult to reach regions, and the surgical procedures performed may necessarily need to navigate narrow and tortuous pathways. Thus, it would be of particular interest to provide devices that are extremely low profile, or are adapted for use with existing low-profile surgical devices and systems. It would also be beneficial to provide devices capable of making multiple, simultaneous cuts at different positions in the tissue (e.g., bone).

Described herein are devices, systems and methods that may address many of the problems and identified needs described above.

SUMMARY OF THE INVENTION

Described herein are devices, systems and methods for cutting predetermined regions of a spine.

In general, the methods described herein include making two cuts through bone in the dorsal spinal column (e.g., through the pedicles, lamina, or other bony regions of the spinal column). The cuts may be made simultaneously (e.g., using a device having two cutting elements which may be arranged in parallel) or sequentially. The method typically begins with the delivery of a guidewire around the target bone region. The guidewire is passed into the body from a first location, around the target bone, and out of the body at a second location. The guidewire may be positioned using one or more needles, cannula, etc. that can steer the guidewire as it is inserted. This method is described in many of the patents incorporated by reference above. The distal end of the guidewire may be sharp, so that it can penetrate the tissue as the guidewire is pushed from the proximal end. The proximal end of the guidewire may be adapted to link securely (and removably) to the distal end of a cutting device, such as a cutting wire saw.

After passing the guidewire around the target bone to be cut, an electrode or other neural localization device (as described in some of the reference incorporated in their entirety above) may be used to confirm that a nerve (e.g., spinal nerve) is not located between the guidewire and the bone to be cut, which could damage the nerve. For example, the distal end of a ribbon-shaped neural localization device (having a relatively flat and flexible profile) may be coupled via a guidewire coupling member to the distal end of the guidewire and pulled into position around the bone, then stimulated by applying electrical current to electrodes on the surface(s) of the neural localization device to confirm that a nerve is not present. If a nerve is present between the target bone and the neural localization device, the guidewire may be removed and repositioned, then the detection process repeated. Other neural localization methods or devices may be used, including visual detection/confirmation of nerve location, detection by electrical impedance measurements, ultrasound, or the like.

Once the guidewire is positioned in the desired pathway to be taken by the cutting element for cutting the bone, a protective element (e.g., cover, shield, etc.) may be positioned by pulling it into position using the guidewire. In some variations the neural localization device is configured as a shield or cover. For example, a shield or cover may be a flat, thin and flexible elongate (e.g., ribbon-shaped) body that can be positioned using the guidewire. The protective element may include a channel or path for the guidewire. In some variations the protective element may be pulled (e.g., pulled distally) into position using the guidewire after coupling the distal end of the protective element to the guidewire, and then the guidewire may be pushed proximally so that the proximal end of the guidewire extends back out of the patient and can be coupled to a second element (e.g., cutting element) while the distal end of the protective device remains in position. In some variations a second guidewire may be passed along the same or a parallel pathway through the tissue to position additional elements such as a cutting element. Channels in/on the protective element may assist with this. Alternatively, in some variations the protective element may be positioned over the guidewire, without coupling to the distal end.

Once the pathway around the target bone to be cut has been determined (and in some variations protected), a cutting tool such a wire saw may then be positioned by coupling the cutting tool to the end of the guidewire and pulling the guidewire to pull the cutting tool (e.g., wire saw) into place. The cutting tool is optimally a thin, flexible cutting tool that may be used bimanually, e.g., by pulling on both the proximal and distal ends of the device to cut the bone. Examples of cutting devices include reciprocating cutting devices, and some examples of these are described below. Cutting elements may be abrasive (e.g., having an abrasive surface). A cutting element may be a wire saw, such as a Gigli saw, as known in the art, which is adapted for use as described herein. Cutting elements are not limited to mechanical cutters. Other cutting elements may include electrical cutting elements, thermal (heat) cutting devices, or the like.

In some variations a separate guidewire is not used, but the cutting element acts as a guidewire. For example, the cutting element may include an integrated guidewire at the distal end. In some variations, the guidewire may be adapted as a cutting element.

Once positioned around the target tissue, the ends of the cutting element may be grasped manually or grasped using an assist device, and the cutting element may be activated (e.g., by manual reciprocation) to cut the bone. Cutting the bone typically means cutting completely through the bone. In variations in which the cutting element is coupled to a guidewire, the cutting element may be reciprocated by pulling on the distal end of the guidewire.

Manual reciprocation of the guidewire may be performed from outside of the patient. The direction of pulling and/or reciprocation may be based on the direction of cutting intended. For example, when it is desirable to cut the bone (e.g., the superior articulating process or SAP) laterally so that the cut extends in the lateral direction relative to the spine, the proximal and distal ends of the cutting element extending from the patient (or the portions of a guidewire or other wire connected to the cutting element that extends from the patient and can be grasped to manipulate the device) are pulled so that the force vector applied by pulling on the two ends at an angle points in the generally lateral direction. In general, the direction of cutting using a flexible wire system as described herein will be determined by the force vector resulting as the ends of the flexible cutting element is pulled from both ends. The pulling force may be alternated—e.g., to reciprocate the cutting element against the tissue.

In some variations, an assist or guide element may be used to help position the cutting element as it is reciprocated against the spine. For example, an assist device or guide may push the cutting element against the tissue, helping to control the direction of the cutting.

The methods described herein may include a device configured to allow simultaneous cutting of two or more bone regions. For example, a device for cutting bone may include two parallel cutting elements that are separated by a predetermined spacer or spaces. The distal and proximal end regions of the cutting elements are connected so that reciprocating the ends of the device will cause reciprocation of both cutting elements. As mentioned, the cutting elements are typically flexible, and may be connected so that they remain separated by a predetermine spacing even when contacting bone or during positioning. For example, the two parallel cutting elements may be separated by a distance of between about 4 and 16 mm, or between about 6-14 mm, or between about 8-15 mm. The two (or in some variations, more than two cutting elements are typically arranged along the long axis (length) of the device. In some variations, the cutting elements may be approximately parallel or actually parallel. In some variation, the cutting elements are not parallel, for example, the cutting surfaces may be slightly angled relative to each other, and the device may be configured so that the distance between the cutting edges may be varied or altered.

In variations in which two or more cuts to remove a portion of bone are made sequentially (rather than in parallel), the method may include cutting the first portion of the bone, then moving the cutting element to the start of the second cut without removing the cutting element from the tissue. Thus, both sides of a cut to remove the bone may be made without removing the cutting element. Cutting a section of bone completely away without having to remove the flexible cutting element (e.g., wire) from the body is one advantage of the methods described herein.

When two cuts are made sequentially as mentioned above, an additional positioning device may be used to push, pull or otherwise guide the middle of the cutting element (e.g., the region looped around the bone) into position around the bone at the desired second cutting position. For example, a wire saw may be used to cut the SAP laterally, then, after cutting completely through the SAP, the bent portion of the cutting element in the tissue may be moved into position by pushing it or sliding it to the second location. An example of this is provided below. The positioning device may be a rigid or stiff member having a distal end configured to push or grasp the loop of the cutting element. Since the bone being cut will be removed, in some variations the procedure includes the step of cutting through the tissue to expose the bone. One or more probes may inserted into this cut and used to position the wire either using a manipulating device once it has been looped around the tissue as desired, or to position the probes to pass the guidewire around the bone to be cut.

Although an opening into the bone may be formed to remove the bone region cut away, it may be beneficial to pass the guidewire around the target bone from a separate (even minimally invasive) access point. Thus, the cut into the tissue to remove the bone may be kept relatively small (e.g., sufficiently large enough only to retrieve the bone that is cut away), while separate pathways for the wire saw may be formed through the tissue in the directions that the wire saw will be reciprocated. In other variations the procedure may be preformed substantially "open," exposing a region of the bone, and allowing manipulation of the ends of the guidewire and/or cutting element as necessary to cut at the desired angles and remove the bone.

In some variations, the methods described herein are adapted for cutting a region of a spinal facet (e.g., cutting on one side of a superior articulating process) specifically, to permit insertion of a device such as a cage or spacer. Described below is a specific example of one procedure and variations of devices that may be used to perform the procedure, as well as systems including such devices. In some variations, the method and devices described herein are adapted for cutting bone to perform an osteotomy. For example, in scoliosis reduction surgery portions of bone are removed to aid in the straightening of the spine. In some variations, the methods and devices described herein are adapted for cutting a spinous process or transverse process or any other suitable portion of bone.

Also described herein are improved devices for modifying tissue and methods of using them. These devices may be included as part of a system for modifying tissue. The tissue modification devices described herein typically include an elongate, flexible length and a tissue modification element coupled to the flexible element. The flexible element may include an expanding mechanism that expands at least a portion of a flexible element from a first width to a second width. A tissue modification device may include one or more of these features in any combination.

Methods for modifying tissue as described herein may include one or more of the following steps: inserting an elongate, flexible element having a first width; advancing the flexible element until a portion of the flexible element is adjacent to a target tissue; expanding at least the portion the flexible element adjacent to the target tissue to a second width; and modifying the target tissue with the flexible element.

The methods for modifying tissue described may alternatively include one or more of the following steps: inserting a first elongate, flexible element into the patient at a first location; advancing the first flexible element until a portion of the flexible element is adjacent to a target tissue; inserting a second elongate, flexible element into the patient at the first location, a distance from the first flexible element; and modifying the target tissue with the flexible elements.

Any of the devices described herein may be used as part of a tissue decompression (e.g., spinal decompression) method to modify tissue such as soft tissue (e.g., ligamentum flavum, etc.) and hard tissue (e.g., bone). In particular, these devices may be used as part of a spinal decompression technique within a spinal foramen.

The devices described herein may be used as part of a guide-based access and decompression system, including those previously described in any of the following patent applications and provisional patent applications, each of which is herein incorporated by reference in its entirety: U.S. patent application Ser. No. 11/250,332, titled "DEVICES AND METHODS FOR SELECTIVE SURGICAL REMOVAL OF TISSUE" (filed Oct. 15, 2005), U.S. patent application Ser. No. 11/251,199, titled "DEVICES AND METHODS FOR TISSUE ACCESS" (Oct. 15, 2005), U.S. patent application Ser. No. 11/375,265, titled "METHODS AND APPARATUS FOR TISSUE MODIFICATION" (filed Mar. 13, 2006), U.S. patent application Ser. No. 11/405,848, titled "MECHANICAL TISSUE MODIFICATION DEVICES AND METHODS" (filed Apr. 17, 2006), U.S. patent application Ser. No. 11/429,377, titled "FLEXIBLE TISSUE RASP" (filed May 4, 2006), U.S. patent application Ser. No. 11/538,345, titled "ARTICULATING TISSUE CUTTING DEVICE" (filed Oct. 3, 2006), U.S. patent application Ser. No. 11/687,548, titled "TISSUE REMOVAL WITH AT LEAST PARTIALLY FLEXIBLE DEVICES" (filed Mar. 16, 2007), U.S. patent application Ser. No. 11/687,558, titled "FLEXIBLE TISSUE REMOVAL DEVICES AND METHODS" (filed Mar. 16, 2007), U.S. patent application Ser. No. 11/870,370, titled "PERCUTANEOUS SPINAL STENOSIS TREATMENT" (filed Oct. 10, 2007), and U.S. patent application Ser. No. 12/127,535, titled "GUIDEWIRE EXCHANGE SYSTEMS TO TREAT SPINAL STENOSIS" (filed May 27, 2008).

In particular, the devices described herein may be used as a guidewire-based system that is configured so that the device may be pulled into position and/or tensioned so as to be urged against a tissue, and thereby modify the tissue. This configuration may be referred to as a bimanual system, since both ends (e.g., the proximal end and the distal end of the device) may be tensioned or pulled to modify the tissue. Tissue may be modified by removal or smoothing of the tissue, and may be performed by pulling the devices described herein through the tissue so that the working surface (e.g., the blades on the rungs) contacts one or more tissue surfaces.

Also described herein are delivery devices for delivering tissue modification devices for removing tissue from a patient. In some embodiments, the device includes a ribbon shaped flexible elongate body having a width defined by a first edge and a second edge. In some embodiments, the first and second edges are substantially parallel. The device may also include a first channel, configured to receive a first elongate cutting member, disposed along a portion of the length of the elongate body, positioned toward the first edge of the elongate body, and a second channel, configured to receive a second elongate cutting member, disposed along a portion of the length of the elongate body, positioned toward the second edge of the elongate body. In some embodiments, the device may also include a guidewire coupler at the distal end region of the elongate body.

In some embodiments, a first flexible elongate cutting member is disposed within the first channel and/or a second flexible elongate cutting member is disposed within the second channel.

Also described herein are methods for delivering tissue modification devices for removing tissue from a patient. In some embodiments, the methods include the steps of inserting an elongate, flexible shield into the patient at a first location; advancing the shield until a portion of the shield is adjacent to a target tissue; inserting a first elongate, flexible cutting element through the shield until a portion of the first cutting element is adjacent to a target tissue; inserting a second elongate, flexible cutting element through the shield, a distance from the first cutting element and substantially parallel to the first cutting element, until a portion of the second cutting element is adjacent to a target tissue; and modifying the tissue with the flexible elements.

In some embodiments, the methods include the steps of inserting a first elongate, flexible cutting element until a portion of the first cutting element is adjacent to a target tissue;

advancing an elongate, flexible shield into the patient, wherein a portion of the shield is advanced over the first elongate, flexible cutting element; inserting a second elongate, flexible cutting element through the shield, a distance from the first cutting element and substantially parallel to the first cutting element, until a portion of the second cutting element is adjacent to a target tissue; and modifying the tissue with the flexible elements. In some embodiments, the methods further include the step of removing the shield from the patient while leaving the cutting elements in position within the patient.

In some embodiments, a bimanually controlled tissue modification device having a tissue modification region for cutting tissue in a patient includes a pair of flexible elongate cutting members extending along the length of the tissue modification region. Each elongate cutting member may have a thickness and each elongate cutting member may be configured to cut a discrete trough into tissue to a depth that is greater than the thickness of the cutting member. In some embodiments, the device includes a guidewire coupler distal to the tissue modification region of the device. The guidewire coupler may be configured to be coupled to a guidewire, e.g., at the proximal end of the guidewire, and the tissue modification region may be actuated by pulling on a proximal handle on or connected to the device, and on a guidewire coupled to the distal end of the device. In some embodiments, the tissue modification region is configured to be actuated by a proximal handle and a distal handle. In some embodiments, the guidewire coupler is configured such that the device is removably attachable to a proximal end region of a guidewire such that the tissue modification region can be pulled into position by pulling on the guidewire while the proximal end region of the guidewire is held stationary by the guidewire coupler with respect to the device. Alternatively, in some embodiments, the device includes a flexible guide at the distal end of the tissue modification device, wherein the guide is configured such that the tissue modification region can be pulled into position by pulling on the guide.

In some embodiments, at least one cutting member comprises a cutting wire, while in some embodiments, at least one cutting member comprises a Gigli wire or an elongate wire having a helical cutting edge along the length of the wire. In some embodiments, at least one cutting member comprises an elongate cable having blade edges distributed along the length of the cable.

In some embodiments, the device includes a spacer coupled to the elongate cutting members of the tissue modification region, wherein the spacer is sized and configured to temporarily hold the cutting members a distance from one another. In some embodiments, the spacer comprises an elongate, flexible, ribbon-shaped substrate and in some embodiments, the spacer includes a coupler toward the outer edge region of the spacer and configured to temporarily secure a cutting member to the outer edge region of the spacer. In some embodiments, the spacer is sized and configured to slide along the length of the elongate cutting members.

In some embodiments, the device further includes a plurality of flexibly connected rungs, wherein each rung extends at least partially across the width of the device. In some embodiments, the rungs are proximal and distal to the tissue modification region of the device. In some embodiments, the device further includes a connector linking adjacent rungs. In some embodiments, the connector may include at least one cable, and in some embodiments, the cable may form the first elongate cutting member and the second elongate cutting member.

In general, a bimanually controlled tissue modification device for cutting tissue in a patient may include a pair of flexible, elongate cutting members extending along the elongate length of the device, and a spacer that may be positioned between the cutting members. In some embodiments, the spacer is sized and configured to operate in one of two modes: a first mode, wherein the spacer is coupled to the cutting members such that it holds a portion of each of the two cutting members a distance from one another across the width of the device; and a second mode, wherein at least a portion of the spacer is moved away from a cutting member to allow the cutting members to cut further into tissue. In the first mode, the spacer(s) may be in the same plane as the cutting member, while in the second mode the spacer(s) may be displaced out of the plane.

In some embodiments, the elongate cutting members are substantially parallel to one another. In some embodiments, the spacer in the second mode is positioned out of the plane of the cutting members. The device may include a guidewire coupler at the distal end region of the tissue modification device. In some embodiments, the spacer in the second mode is positioned such that each of the cutting members can cut a depth into tissue that is greater than the thickness of the cutting members. In some embodiments, the spacer further comprises a coupler configured to couple the spacer to a cutting member while the spacer is in the first mode. In some embodiments, the spacer transitions from the first mode to the second mode as the cutting member cuts through the coupler. In some embodiments, the spacer transitions from the first mode to the second mode as the coupler slides along the length of the elongate cutting member. Any appropriate number of spacers may be used. The same device may use different types or configurations of spacers.

In some embodiments, the coupler may be a deformable material sized and configured such that the spacer transitions from the first mode to the second mode as the deformable material deforms and a portion of the spacer moves with respect to the cutting member. In some embodiments, the device further includes a spring, wherein the spring is configured to expand as the spacer transitions from the first mode to the second mode. In some embodiments, the cutting members are sized and configured to cut a first depth into the tissue while the spacer is in the first mode and to cut a second, greater depth into the tissue while the spacer is in the second mode. In some embodiments, the cutting members are configured to be actuated by a proximal handle and a distal handle. The cutting members may be reciprocated, for example, they may be pulled distally by a distal handle and pulled proximally by a proximal handle.

In general, a method of modifying tissue may include the steps of passing an elongate, flexible tissue-modification device at least partially around a target tissue; moving a tissue-modification region of the device against the target tissue by pulling the tissue-modification device from at least one end of the device; and cutting two discrete elongate troughs into the tissue with a pair of flexible elongate cutting members extending along the elongate length of the tissue modification region. For example, the elongate cutting members may have a thickness (e.g., between about 0.01 cm and about 5 cm) and each of the elongate troughs may be cut to a depth that is greater than the thickness of the cutting members. In some embodiments, the elongate troughs each have a depth greater than 1 cm. In some embodiments, the elongate troughs each have a depth greater than 2 cm. In some embodiments, the elongate troughs are substantially parallel to one another.

As mentioned, the troughs are typically discrete, and separated from each other. In some variations, the troughs may join or meet as the device continues to cut into the tissue (e.g., bone). The spacing between the troughs may be predetermined (e.g., 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, etc.), which may correspond to the spacing between cutting elements on the cutting device.

In some embodiments, the method further includes the step of removing the target tissue. The target tissue may comprise at least a portion of a facet joint. In some embodiments, the step of passing the tissue-modification device at least partially around the target tissue comprises passing a guidewire at least partially around the target tissue and pulling the flexible tissue-modification device around the target tissue using the guidewire. In some embodiments, the cutting step includes the steps of cutting the troughs to a first depth into the tissue with a pair of flexible elongate cutting members held a distance from one another with a spacer and cutting the troughs to a second, greater depth into the tissue with the pair of flexible elongate cutting members.

The spacer may be moved with respect to the cutting members before cutting the troughs to the second, greater depth. In some embodiments, the method includes the step of collecting cut tissue with the spacer as the spacer moves away from the cutting members. The step of moving the tissue-modification device against tissue may comprises applying tension to both the proximal end and the distal end of the tissue-modification device to drive the tissue-modification device against the tissue either simultaneously or sequentially (e.g., reciprocating it).

In some embodiments, the method includes the step of cutting through a coupler with at least one of the cutting members while cutting the troughs, wherein the coupler couples a spacer to the cutting member. In some embodiments, the method includes the step of detaching at least one of the cutting members from a coupler while cutting the troughs into the tissue, wherein the coupler couples a spacer to the cutting member. In some embodiments, the cutting step further comprises reciprocating the tissue-modification region of the device against the target tissue by pulling the tissue modification region distally with a distal handle and by pulling the tissue modification region proximally with a proximal handle.

BRIEF DESCRIPTION OF THE DRAWINGS

FIGS. 16A-18D illustrate tissue modification devices having spacers.

FIG. 30A illustrates a cross-section through one variation of a facet-joint modifying device that includes two bone-sawing elements.

FIG. 30B illustrates a cross-section through one portion of the device having a breakable spacer.

FIG. 30C shows a top view of one variation of a facet-joint modifying device configured to perform a facetectomy.

FIGS. 31A-31E illustrate variations of joint treatment devices. In FIG. 31A, the treatment device includes a front and a back articulating surface that can be drawn across the joint surfaces to roughen them; FIGS. 31B-31D show different cross-sections through joint treatment devices, and FIG. 31E illustrates another variation of a joint treatment device. Any of these joint treatment devices may be facet joint treatment devices.

DETAILED DESCRIPTION OF THE INVENTION

Described herein are devices, systems and methods for cutting spinal tissue such as bone and/or soft tissue, and particularly spinal bone in the dorsal column using a flexible cutting element that may be passed around the bone. In some embodiments, these devices, methods and systems may be used to cut two substantially parallel cuts into tissue without requiring the removal of the cutting element between cuts. The methods, devices and systems described herein may be used as part of a spinal surgical procedure involving a complete or partial removal of spinal bone or joint, such as a laminectomy, laminotomy, fascetectomy, pediculectomy, etc.

Figure 1A:
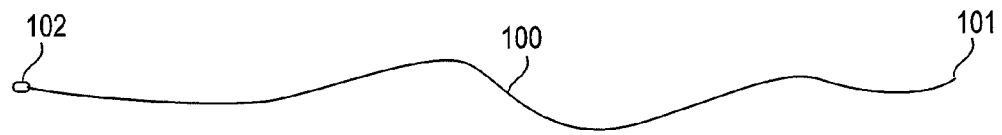
FIGS. 1A-1D illustrate elements that may be used for performing the methods described herein; some or all of these elements (the guidewire of FIG. 1A, neural localization device of FIG. 1C, flexible wire saw of FIG. 1B, and parallel wire saw of FIG. 1D) may form a system for cutting tissue.

FIGS. 1A-1D illustrate different elements that may be used as part of a system for cutting bone as described. FIG. 1A shows a guidewire 100 that is adapted to couple to the distal end of another device so that the device may be pulled into position using the guidewire. The distal end 101 of the guidewire may be sharp, and the proximal end may include a coupling joint 102 (e.g., a ball or other enlarged region that can be gripped by a coupling member).

Figure 1B:
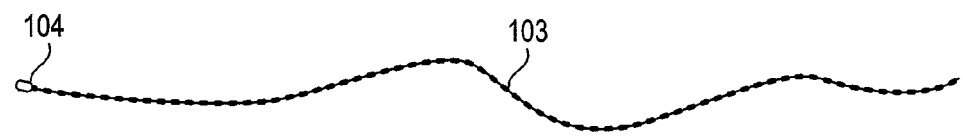

FIG. 1B shows one variation of an elongate cutting member, such as a cutting wire 103 having an abrasive surface for cutting tissue, such as soft tissue (e.g. ligament) and/or bone. Such saw wires (e.g., traditional Gigli saws) may be adapted for use with a guidewire. For example, the distal end of the saw may include a guidewire coupler 104. In some variations the wire is thin or flattened. Any appropriate saw or cutting element may be used, including those that cut by reciprocation or by application of energy.

Figure 1C:
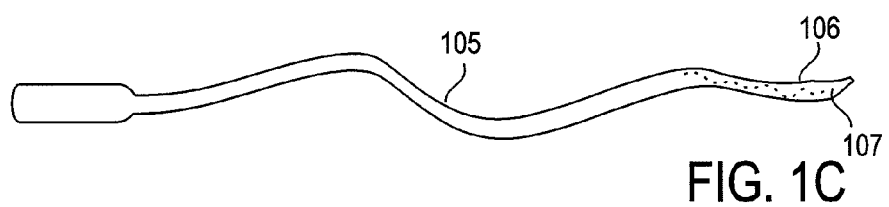

FIG. 1C illustrates one variation of a flexible ribbon-shaped neural localization device 105. The distal end 106 of the device is substantially flat (not apparent from the figure) and has flat sides with one or more electrodes 107 along the surface to stimulate a nerve or neural tissue, if nearby.

Figure 1D:
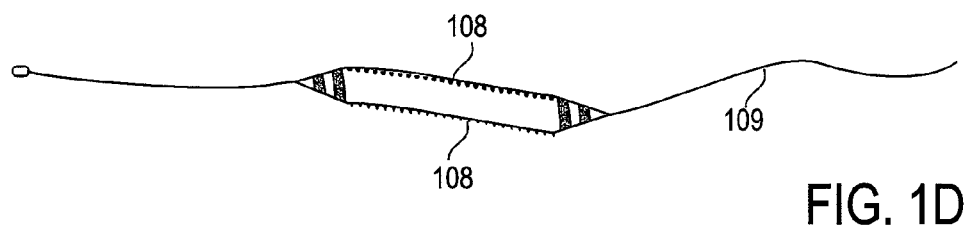

FIG. 1D illustrates another variation of a bone saw device having two parallel cutting wires 108 that are separated by a predetermined distance (e.g., 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, etc.). The distal end of the device may be configured for coupling to a guidewire 100. Alternatively, the device may have an integral flexible guide region 109 at the distal end of the device so that the device does not need any additional guidewire/coupler. For example, flexible guide region 109 is shown having a curved shape to demonstrate that at least a portion of flexible guide region 109 may be flexible. The distal portion is preferably flexible in at least one direction, such that it may wrap around a target tissue, while having sufficient column strength such that the distal end may penetrate tissue without budding. In some embodiments, the distal end may have a sharp distal tip configured to penetrate and/or pierce tissue. In various embodiments, flexible guide region 109 may have one or more of a round, ovoid, ellipsoid, flat, cambered flat, rectangular, square, triangular, symmetric or asymmetric cross-sectional shape. Distal flexible guide region 109 may be tapered, to facilitate its passage into or through narrow spaces as well as through small incisions on a patient's skin. Distal flexible guide region 109 may be long enough to extend through a first incision on a patient, between target and non-target tissue, and out a second incision on a patient. In some embodiments, the distal end may have a length greater than or equal to 3 inches such that it may extend from around the proximal end of the stimulation region to outside the patient where it may be grasped by a user and/or a distal handle. In some alternative embodiments, the distal end may have a length greater than or equal to 10 inches while in some other alternative embodiments, the distal end may have a length greater than or equal to 16 inches. Alternatively, distal flexible guide region 109 may be long enough to extend through a first incision, between the target and non-target tissue, and to an anchoring location within the patient.

Figure 2:
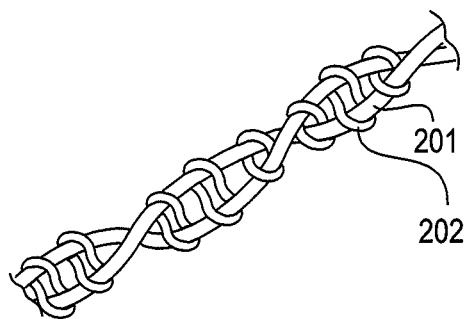
FIGS. 2-3D show various embodiments of a cutting wire.
Figure 3A:
Figure 3B:
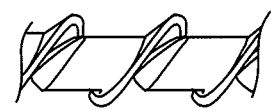
Figure 3C:
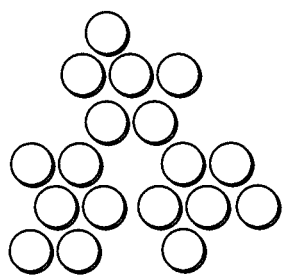
Figure 3D:
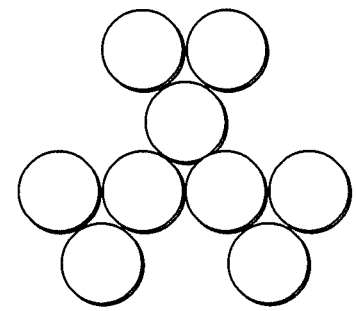

The cutting wires 108 as described herein may be one of several variations of cutting wires. In some embodiments, the cutting wires may have an outer diameter that ranges from 5 to 50 thousandths of an inch, for example. A single wire saw may include a plurality of wires wrapped around each other at differing pitches. As shown in FIG. 2, wire 202 having a first diameter, may be wrapped around wire 201 having a second diameter. As shown, the first diameter may be less than the second diameter. FIG. 2 illustrates one example of a Gigli cutting wire. Alternatively, as shown in FIGS. 3A-3D, the cutting wire of the tissue modification device can be one of several alternative embodiments. For example, as shown in FIG. 3A, the cutting wire may be a second embodiment of a conventional Gigli wire. A Gigli wire is typically made of a first wire having a first diameter wrapped around a second wire having a second diameter. Typically, the second diameter is larger than the first diameter, but alternatively, they may have substantially the same diameter, as shown in FIG. 3A. In some embodiments, a first set of first and second wires may be wrapped around a second set of first and second wires. Alternatively, as shown in FIG. 3B, the cutting wire may include a single wire that is machined to include a helical or spiral cutting edge along the length of the wire. This wire may be machined by cutting a spiral or helical groove along the length of the wire. As shown in FIGS. 3C and 3D, the cutting wires may be formed by winding bunches of wires. For example, as shown in cross section in FIG. 3D, the cutting wire may comprise a 3 by 3 construction. In this embodiment, three wires are first wrapped around one another to create a first bunch of wires. Then three sets of those three wire bunches are subsequently wrapped around each other. As shown in cross section in FIG. 3C, rather than initially wrapping three wires together, 6 wires may be wrapped together to create a bunch of wires and then three sets of the 6 wire bunches may be wrapped together to form a 3 by 6 configuration. Each 6 wire set may be formed as a 7 wire set might be formed, but leaving one wire position empty.

Figure 4:
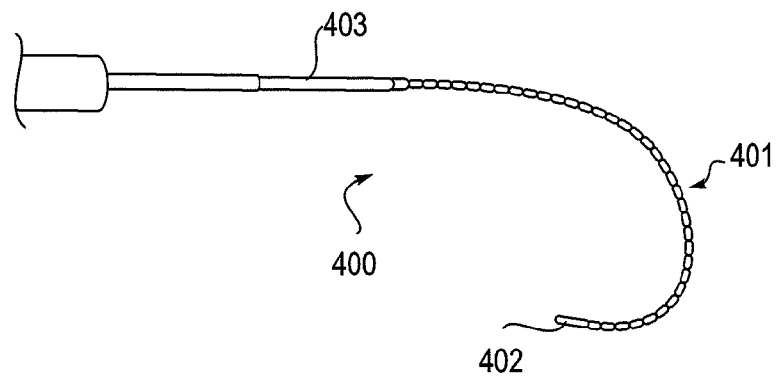
FIG. 4 illustrates a tissue modification device having a cutting wire.

As shown in FIG. 4, a tissue modification device 400 includes a tissue modification portion 401, a distal end 402, and a proximal end 403. The tissue modification portion may include a wire saw configured to cut through bone and/or soft tissue. The distal end 402 may include a guidewire coupler. The proximal end 403 may be more rigid than the flexible tissue modification region 401. The proximal end may be coupled to a proximal handle used to grasp, position, and/or reciprocate the tissue modification device.

Figure 5:
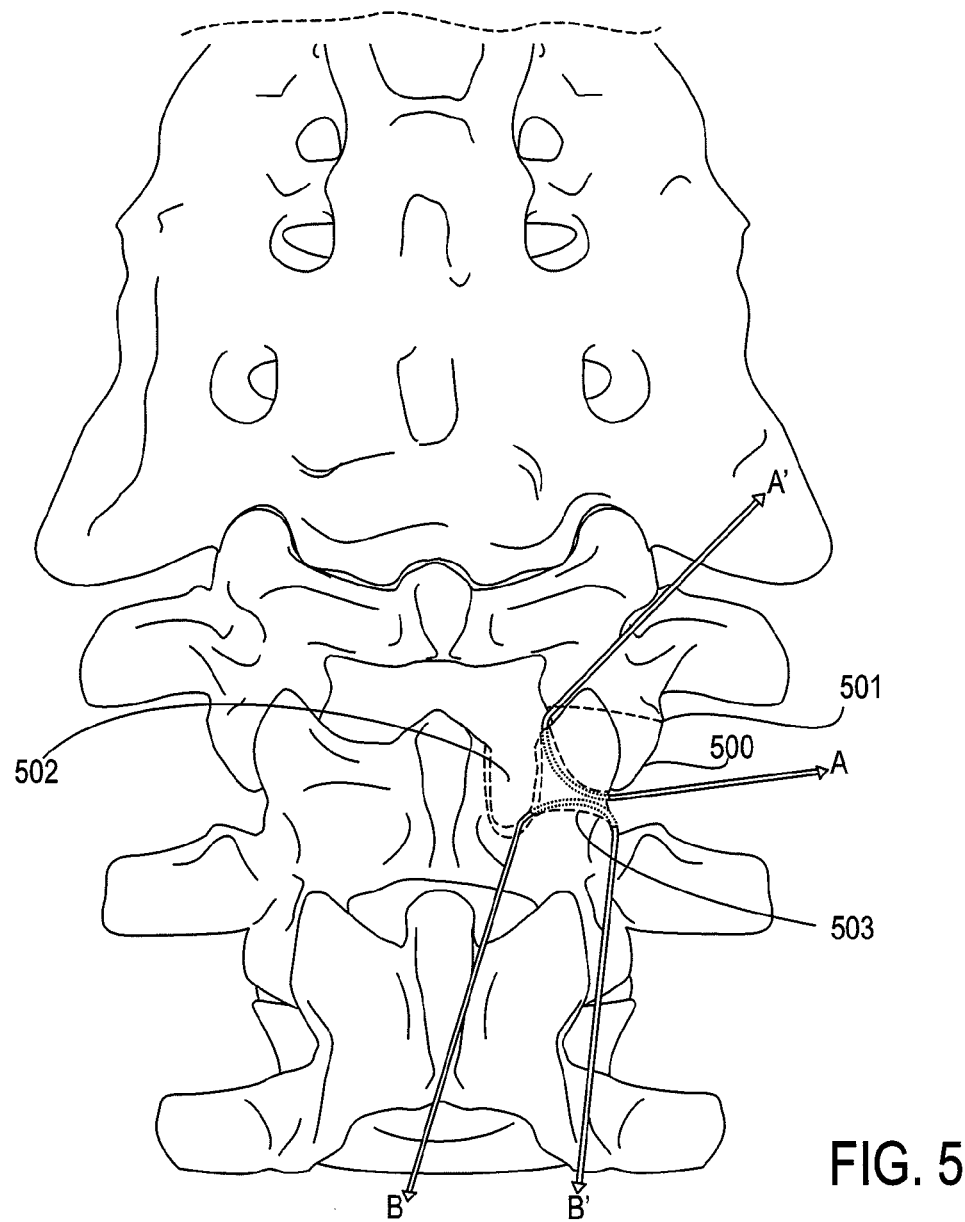
FIG. 5 illustrates a method for cutting a lateral portion of a facet.
Figure 6A:
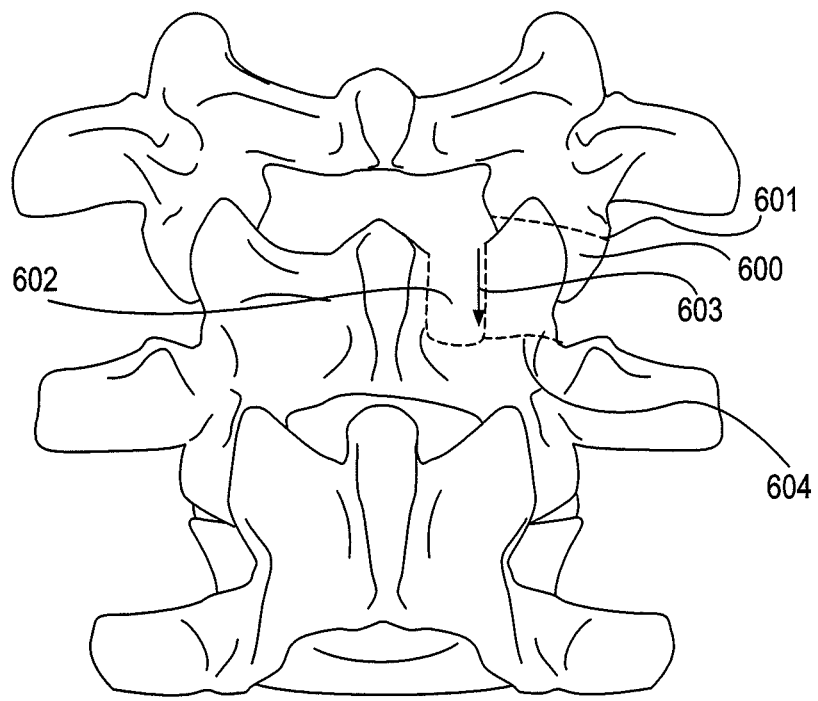
FIG. 6A illustrates a variation of a method for cutting the lateral portion of a facet.
Figure 6B:
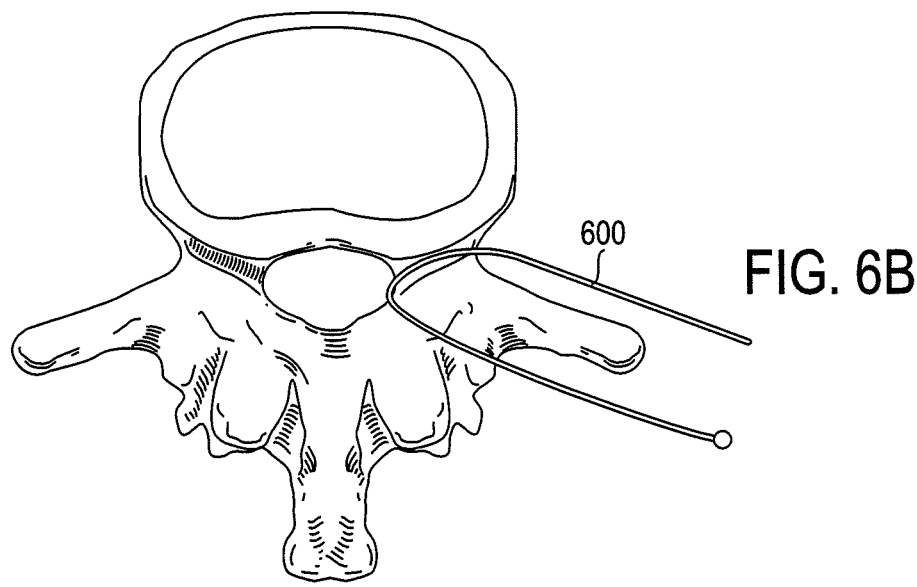
FIG. 6B illustrates one step of a method for cutting a facet.

In operation, the devices described above may be used as part of a system for cutting bone, as illustrated in FIGS. 5-6B. In this example, the facet is cut laterally, which may be used as part of a TLIF procedure, for example. FIG. 5 shows an overview of this method. In this example, two cuts through the bone are made sequentially. To cut the facet joint as desired for this procedure, a guidewire is first positioned partially around/against a superior articular process (SAP) 500 that will be cut. The guidewire may be positioned using or more probes or cannula so that the guidewire enters laterally from a first position (A) passes through the foramen and around the SAP 500, and leaves the spine (and exits the patient) at a second position (A'). Once the guidewire is positioned, it may be used to pull in a neural localization device to confirm that a nerve (spinal nerve or nerve root) is not between the bone to be cut and the pathway of the guidewire. After confirmation that the nerve is not between the bone and the pathway, a cutting element (e.g., wire saw 1B) may be pulled into position so that both the distal and proximal ends of the wire saw exit the patient and may be pulled upward (in the posterior direction) and reciprocated laterally to cut the SAP as indicated by the dashed line 501 in FIG. 5.

Once the SAP has been cut by the saw, the saw may then be positioned for the second cut, through the lamina. Optionally, before this cut is made, and before the wire saw is moved to this location, the lamina may be prepared by notching or biting away portion of the lamina 502 with a Rongeur or other device (e.g. forming a laminotomy). For example, in FIG. 5, the dotted region shows an area 502 that may be bitten away to form a partial window into the lamina. Once that is done, the cutting element (wire saw) is moved in the cephalid direction (down in the orientation of FIG. 5), so that the ends of the wire extend in the cephalid direction (and across the central spinal axis). Thus, one end of the saw B is present in the notch or window formed in the lamina, and the other end B' moves along the foramen. If desired, the neural localization device may again be used to confirm that a nerve will not be cut from this position, e.g., by retracting the guidewire proximally, removing the cutting element and attaching the neural localization device. Finally, the cutting element may be reciprocated to cut through the pars region of the lamina along dotted line 503. Thereafter the cut away portion of the bone may be removed, and other procedures performed as desired.

In the embodiments including two parallel wires, the facet or target tissue suture may be cut in a single step. For example, to perform a Facetectomy, the device may be deployed just cephalad of the caudal pedicle. The parallel wires may be held at the desired width, or the wires may be expanded to the desired width. The desired width may range from 6 mm-15 mm, depending on the interbody device to be inserted between the vertebras, for example. In some variations, the cephalad wire may be expanded to the desired width. The device may then be reciprocated across the tissue to cut through and remove at least a portion of the width of the facet joint. The device may be reciprocated by alternatively pulling a proximal end of the device (e.g. proximal handle) and pulling a distal end of the device (e.g. a distal handle and/or or guidewire). While one end is pulled, the other end may also be pulled to maintain tension across the device.

FIGS. 6A and 6B illustrate alternative views of the steps described above. For example, FIG. 6A shows the steps of cutting through the SAP 600 (dotted line 601), biting away/forming a window 602 in the lamina, moving the cutting element in the caudal direction (arrow 603) and cutting the pars (dotted line 604). FIG. 6B shows a cross-sectional view through the spine indicating the cutting of the SAP. As shown, the cutting wire 600 is positioned through the foramen and around the SAP (not shown). The wire will be reciprocated and pulled in the direction of the arrows to cut through the SAP.

As mentioned above, in any of the facet joint procedures described herein, all or a portion of the facet (e.g., the superior and/or inferior spinous processes) may be cut. For example, a procedure for fusing or preparing a facet joint may include a facetectomy, particularly for TLIF (Transforaminal Lumbar Interbody Fusion) procedures. The procedure may include a facet joint treatment device that is configured to saw through bone. For example, the device may include one or more cable-type saws including a distal end that is configured to couple to the pull wire as described above. As mentioned, a probe or probes may be used to place the pull wire under the facet joint. A facet joint modifying device may then be pulled in under bimanual control. Pulling the facet joint modifying device dorsally (e.g., by distal/proximal reciprocation) would result in the removal of the entire facet joint. This method may be faster than current methods which involve slow biting with Rongeur-type devices.

Tissue Modification Device Having Two Elongate Cutting Members

In some embodiments of the devices, systems and methods for cutting tissue in a patient described herein, a tissue modification region of a device includes a pair of flexible elongate cutting members extending along the length of the tissue modification region. Each elongate cutting member may be configured to cut a separate trough into tissue to a depth that is greater than the thickness of the cutting member.

Figure 7:
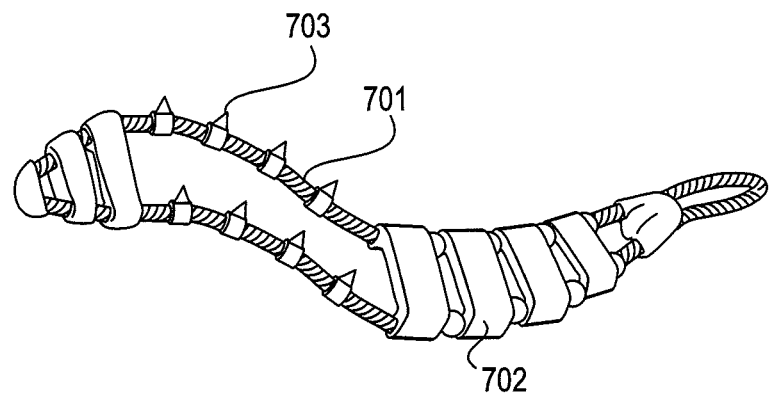
FIGS. 7-11 illustrate variations of a tissue modification device having a pair of elongate cutting members.

In a first embodiment, the tissue modification device (e.g., bone saw) may include cutting edges directly coupled to a cable, as shown in FIG. 7, the cable 701 may include cutting elements 703 such as beads, blades, wires, or other suitable cutting elements. In some embodiments, the cutting elements may be crimped onto the wire or attached by other suitable methods. The cutting cables may cut tissue using an energy such as heat or radio frequency energy. The energy may function to desiccate and/or shrink the tissue, rather than cutting it. As shown in FIG. 7, a portion of the device may include cutting cables 701, while a portion of the device includes spacers or rungs 702 threaded onto cables (with or without cutting edges on the spacers). The cutting cables and the cables onto which the spacers are threaded may be the same or different cables.

Figure 8:
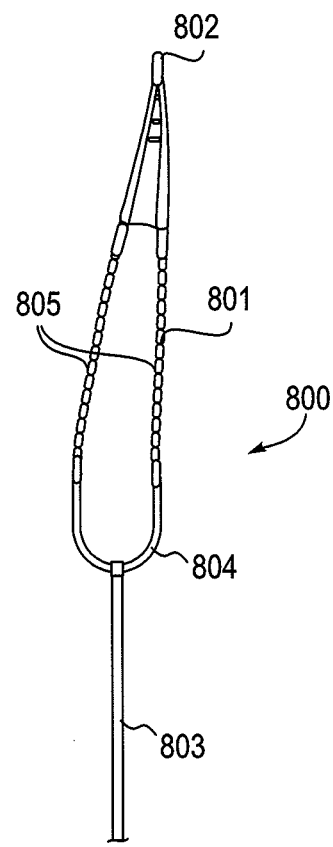
Figure 9:
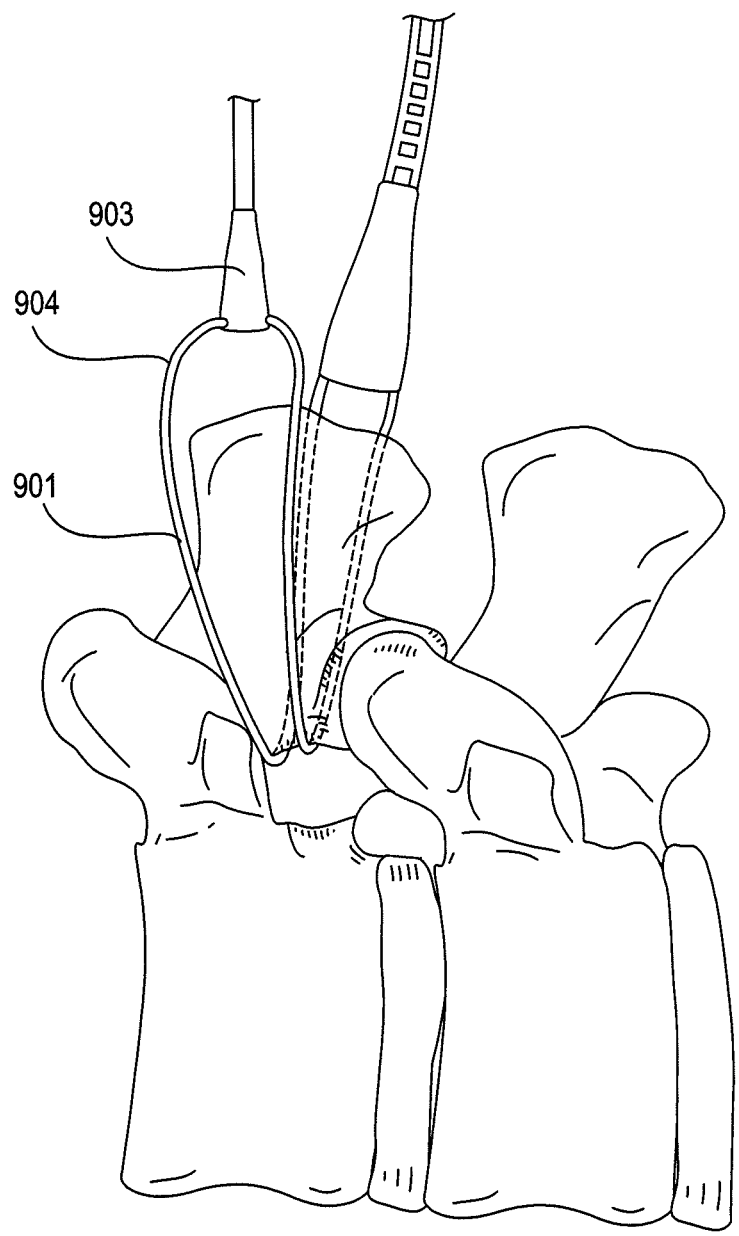
Figure 10:
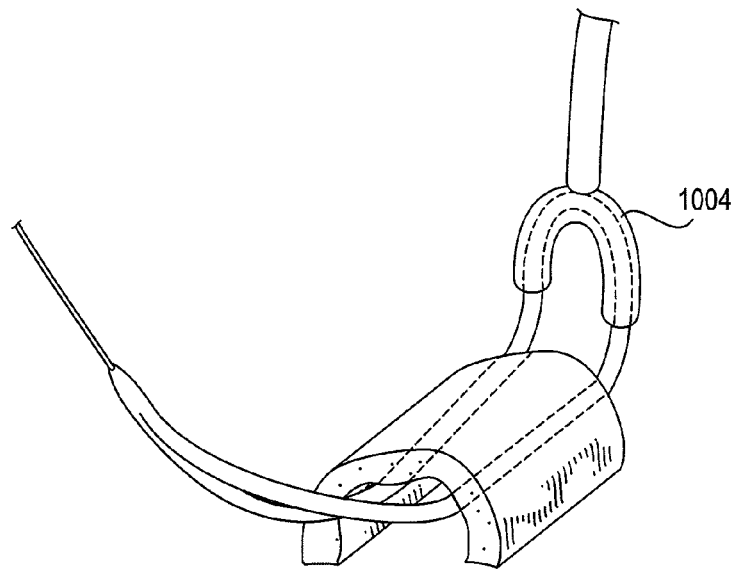

As shown in FIG. 8, a tissue modification device 800 includes a tissue modification portion 801, a distal end 802, and a proximal end 803. The tissue modification portion may include two parallel wire saws 805 configured to cut through bone and/or soft tissue. The distal end 802 may include a guidewire coupler. The proximal end 803 may be more rigid than the flexible tissue modification region 801. The proximal end may be coupled to a proximal handle used to grasp, position, and/or reciprocate the tissue modification device. The proximal end 803 may include a proximal connector element 804 that couples the proximal end 803 to the parallel wire saws 805. In some embodiments, the tissue modification portion 801 may include a single wire saw that is coupled at one end to the distal end, fed through the proximal connector element 804, and coupled at a second end to the distal end. The cutting wire may be configured to slide through the proximal connector element and to be movable with respect to the proximal end 803. FIG. 9 shows the tissue modification device positioned within a spine. As shown, the surfaces of the spine about which the device is positioned may be uneven. In some instances, the device may not contact the surfaces of the spine in a balanced way, or may not be taut against the surface to be cut. As shown in FIGS. 9 and 10, the proximal connector element (labeled 904 and 1004, respectively) ensures that the cutting wire can slide through the connector element and be repositioned such that both parallel portions of the cutting wires can be taut against the tissue to be cut.

Figure 11:
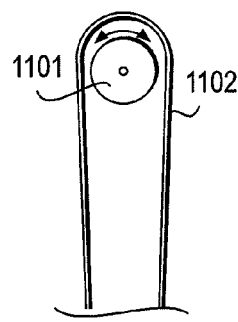

In an alternative embodiment, as shown in FIG. 11, the tissue modification device may include a pulley 1101. The pulley is coupled to the cutting wire 1102 and may be positioned at the proximal and/or the distal end of the tissue modification device. The pulley may be configured to reposition the cutting wire such that both parallel portions of the cutting wires can be taut against the tissue to be cut.

Figure 12:
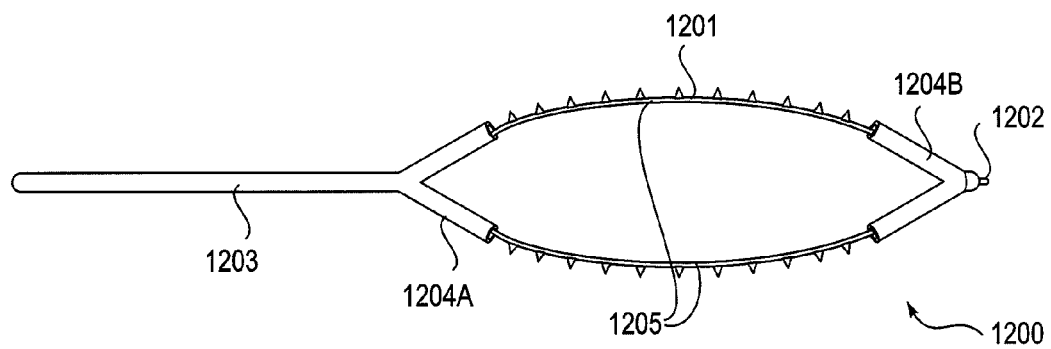
FIGS. 12-14B illustrate tissue modification devices having shaped wires.

As shown in FIG. 12, a tissue modification device 1200 includes a tissue modification portion 1201, a distal end 1202, and a proximal end 1203. The tissue modification portion may include two parallel wire saws 1205 configured to cut through bone and/or soft tissue. The distal end 1202 may include a guidewire coupler. The guidewire coupler may be coupled to a guidewire (which may be coupled to a distal handle) and may be used to grasp, position, and/or reciprocate the tissue modification device. The proximal end 1203 may be more rigid than the flexible tissue modification region 1201. The proximal end may be coupled to a proximal handle used to grasp, position, and/or reciprocate the tissue modification device. The proximal end 1203 may include a proximal connector element 1204A that couples the proximal end 1203 to the parallel wire saws and the distal end 1202 may include a distal connector element 1204B that couples the distal end 1202 to the parallel wire saws. In some embodiments, the tissue modification portion 1201 may include a single wire saw that is fed through the proximal connector element 1204A and the distal connector element 1204B. The cutting wire may be configured to slide through the connector elements. As shown, the connector elements are configured to hold the cutting wires apart from one another. In some variations, the wires are held a distance apart that is greater than the minimum desired width such that if some approximation of the cutting wires 1205 does occur during positioning and/or reciprocation of the device (due to the geometry and/or or anatomy of the spine, for example), the wires will still be at least the minimum desired width apart. In some variations, the connector elements are made from a flexible or shape memory material such as Nitinol. In this variation, if the connectors are compressed, such that the leg portions of the connectors are brought closer to one another, the connector legs will be biased apart and will return to their original configuration.

Figure 13A:
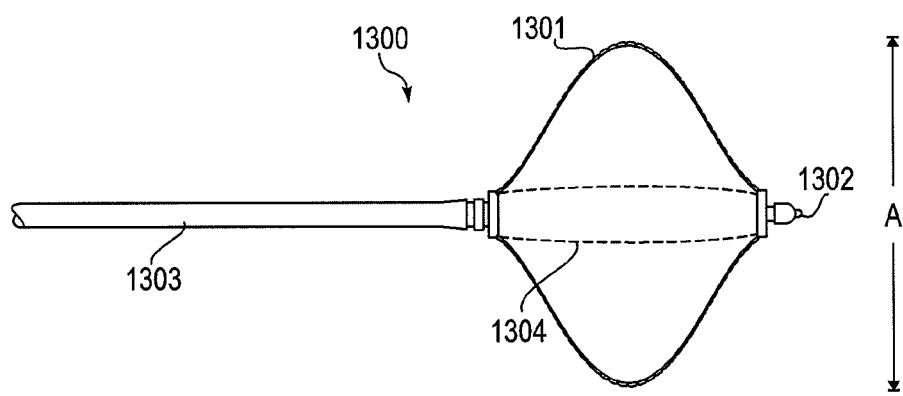
Figure 13B:
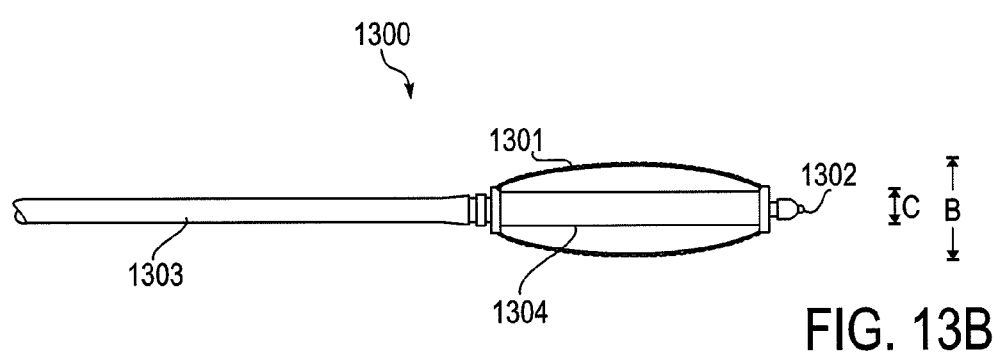

In an alternative variation, as shown in FIGS. 13A and 13B, a tissue modification device 1300 includes a tissue modification portion 1301, a distal end 1302, and a proximal end 1303. The tissue modification portion may include two parallel wire saws configured to cut through bone and/or soft tissue. The distal end 1302 may include a guidewire coupler. The guidewire coupler may be coupled to a guidewire (which may be coupled to a distal handle) and may be used to grasp, position, and/or reciprocate the tissue modification device. The proximal end 1303 may be more rigid than the flexible tissue modification region 1301. The proximal end may be coupled to a proximal handle used to grasp, position, and/or reciprocate the tissue modification device. In some variations, the cutting wires are made from a flexible or shape memory material such as Nitinol. As shown in FIG. 13A, the wires in their equilibrium or biased configuration are held a first distance A apart. Distance A is wider than a minimum desired width. In this variation, if the cutting wires are compressed, such that the cutting wires are brought closer to one another, the cutting wires will be biased apart and will return to their original, wider configuration. As described, the wires are held a distance apart that is greater than the minimum desired width such that if some approximation does occur, the wires will still be at least the minimum desired width apart. In operation, a guidewire may be coupled to distal end 1302 such that the tissue modification device can be alternatively pulled by the guidewire and the proximal end of the device. As shown in FIG. 13B, as the device is pulled and reciprocated, it is possible that the wires will approximate toward one another to a width B as the tissue modification portion 1301 is elongated. Width B is preferably at least as wide as the minimum desired width. In some variations, the device may further include a length limiting element 1304. As shown in FIG. 13A, the length limiting element is flexible and not pulled taut. In FIG. 13B, as the device is pulled and reciprocated, the tissue modification portion 1301 is elongated only to the length of the length limiting element 1304. The length limiting element 1304 is configured such that the tissue modification portion 1301 cannot be elongated such that width B is too small. Width B is preferably at least as wide as the minimum desired width. Alternatively, in some variations width C is preferably at least as wide as the minimum desired width.

Figure 14A:
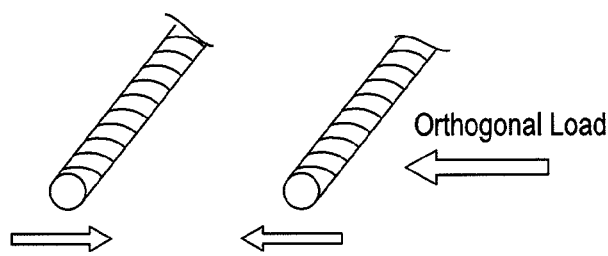
Figure 14B:
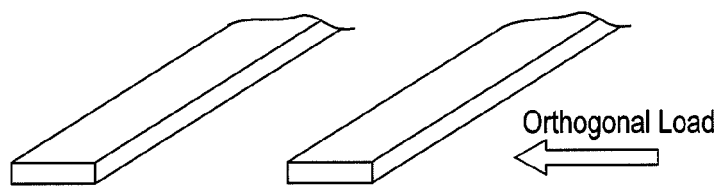

In some embodiments, as shown in FIGS. 14A and 14B, the cutting wire may have a cross section that is configured to limit the flexibility in the orthogonal direction and therefore limit approximation of the wires. As shown in FIG. 14B, the wider, substantially rectangular cross section is less susceptible to an orthogonal load as shown.

Tissue Modification Device Having a Spacer

In some embodiments, a tissue modification region of a cutting device includes a pair of flexible elongate cutting members extending along the length of the tissue modification region and also includes a spacer. Each elongate cutting member may be configured to cut a discrete trough into tissue to a depth that is greater than the thickness of the cutting member. A spacer may generally span the width between the two cutting members holding them some predetermined (or adjustable) distance apart. Since the spacers do not typically cut the tissue, they may be configured so that they do not substantially inhibit the cutting gwires or edges from cutting the tissue. The spacer may be sized and configured to operate in one of two modes. A first mode, in which the spacer is coupled to the cutting members such that it holds a portion of each of the two cutting members a distance from one another, and a second mode, in which at least a portion of the spacer is moved away from a cutting member to allow the cutting members to cut further into tissue.

Referring again to FIG. 9, in some embodiments, the uneven or curved surfaces of the spine may cause the elongate cutting members 901 to approximate at the apex of the curve and/or the anterior portion of the facet joint, for example. If the wires approximate to a substantial degree, the width of tissue cut and/or removed by the device may not be as wide as desired or required for the specific procedure. For example, if the wires are too close to one another, they may not be able to cut around the facet joint and the entire facet joint may not be removed. In these cases, it may be advantageous to provide a tissue modification device further including a spacer, as described in detail below.

Figure 15:
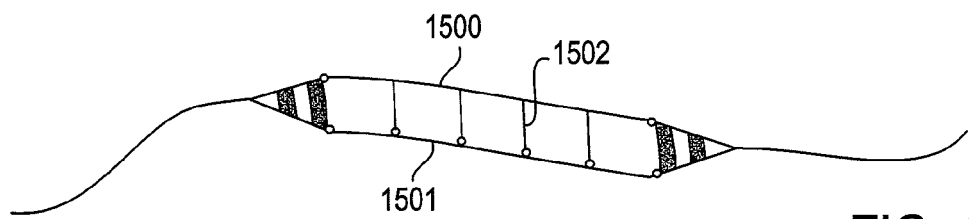
FIG. 15 shows another variation of a tissue modification device having a pair of elongate cutting members.

FIG. 15 shows another variation of a parallel wire saw, in which the parallel wires 1500 and 1501 are held a minimum distance apart. Thus, although the device is flexible, it is desirable to have the distance between cutting wires (and thus the width of the bone chunk being cut away) a predetermined length apart. In FIG. 15, one or more spacers 1502 may hold the cutting wires apart. The spacers may be removed (e.g., by breaking away or by separating from one side of the device) during reciprocation, or they may be expandable (but not very compressible) so that they may allow the cutting regions to bite into the bone while expanding.

Figure 16A:
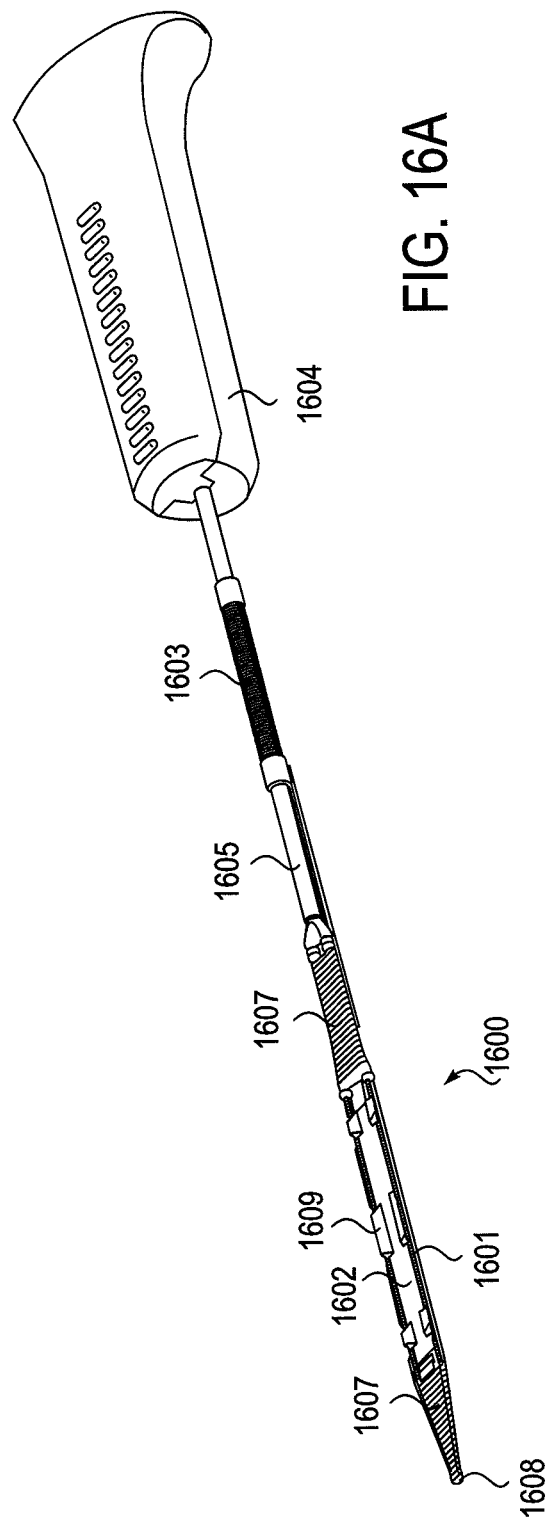

FIGS. 16A-18D illustrate an alternative embodiment of a tissue modification device 1600 having a pair of flexible elongate cutting members 1601 and a spacer 1602. As shown in FIG. 16A, the tissue modification device includes a distal end having a tissue modification region and a proximal end 1605 having, in some embodiments, a proximal handle 1604. The distal tissue modification region includes the pair of flexible elongate cutting members 1601 and the spacer 1602. As shown, a guidewire coupler 1608 may be at the distal end of the tissue modification device. The guidewire coupler may be configured to attach to a guidewire (e.g., the proximal end of a guidewire) so that the device can be manipulated (e.g. reciprocated), at least in part, by pulling on the guidewire after the guidewire has been secured to the device. As shown in FIG. 16A and in greater detail in FIG. 16B, the spacer 1602 may further include passive restraints 1609 coupled to the outer edges of the spacer. As shown, portions of these restraints are coupled to cutting member 1601. These restraints may function to hold the cutting wires toward the outer edges of the device and/or prevent the wires from approximating. As shown, the restraints may not run the entire length of the tissue modification region of the device. This may be desirable such that a portion of the cutting wires 1601 are exposed. These exposed wires may provide cutting action during the initial reciprocations of the tissue modification device against the tissue. As the device is pulled back and forth (i.e. reciprocated) across the tissue, the exposed portions of the cutting wires 1601 will begin to cut through the bone and/or soft tissue. In some embodiments, the device is pulled "up" (toward the back of the patient) and against the tissue while the device is reciprocated across the tissue. Due to this upward pressure, the cutting wires will begin to cut into the tissue and create troughs into the tissue. As the initial troughs are formed in the tissue, and the cutting wires move deeper into the tissue, the cutting wires will eventually detach from the restraints 1609. In some embodiments, the restraints are made from an elastic or otherwise deformable material such that the upper lip (labeled 1707 in FIG. 17B) of the restraint can deform to allow the cutting wire to pull out of the restraint. Alternatively, the cutting wire may cut through or break off a portion (e.g., the upper lip) of the restraint.

Returning to FIG. 16A, the tissue modification device further includes a spring 1603. This spring may function to couple the shield 1602 to the proximal end 1605 of the tissue modification device. As the cutting wires 1601 cut into the tissue, and the spacer 1602 moves away from the cutting wires, the spring 1603 will stretch and allow the proximal end of the spacer (labeled 1802 in FIGS. 18A-18C) to move toward the distal end of the device such that the distal end of the spacer may bend and move away from the cutting wires 1601. Also, as shown in FIG. 16A, the tissue modification device may optionally include rungs 1607. These rungs may thread over the wires that run the length of the device. The rungs may be positioned distal and/or proximal to the tissue modification region of the device. In some embodiments, the spacer may be connected to a rung(s) positioned distal to the tissue modification region.

Figure 16B:
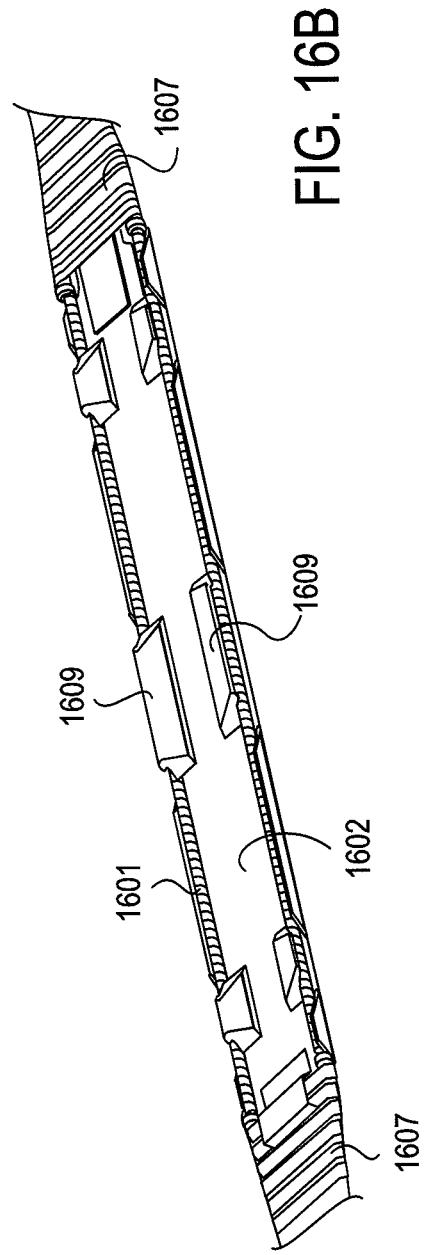
Figure 17A:
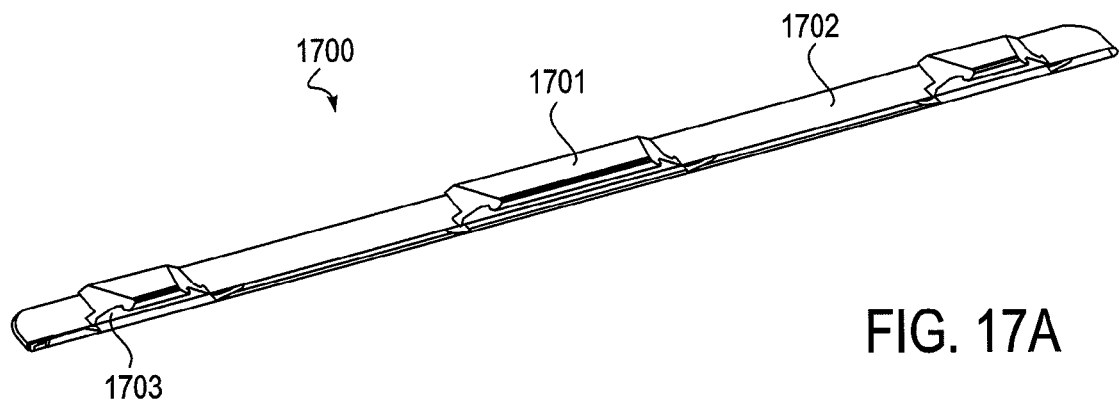
Figure 17B:
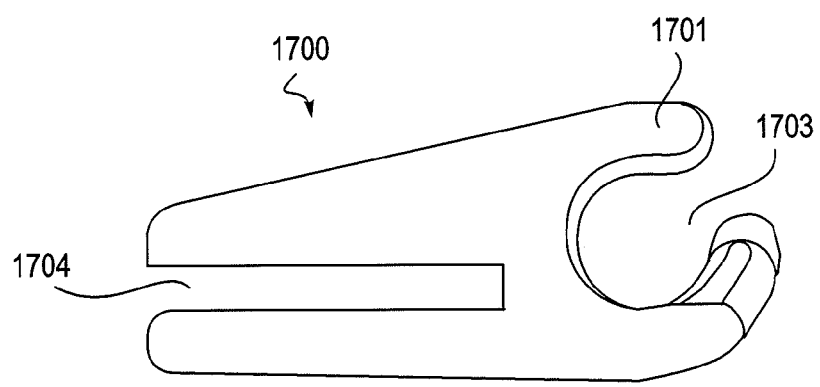

FIGS. 17A and 17B illustrate in detail the passive restraint 1700 as described above. As shown in FIG. 17A, the restraint includes an upper lip portion that couples to the cutting wire and temporarily holds the cutting wire in position, a distance from the other cutting wire. The upper lip defines channel 1703 in which the cutting wire may be temporarily held. The restraint also includes a base portion that may function to couple the restraint 1700 to the spacer of the tissue modification device. As shown in FIG. 17B, the base portion 1702 of the restraint may define channel 1704. This channel may be sized and configured to receive the outer edge of the spacer. As shown in FIG. 16B, the spacer may include two passive restraints, one coupled to each edge of the spacer. In some embodiments, the restraint may extruded or molded and then may be coupled to the spacer using adhesive, UV glue, or any other suitable coupling mechanism. Alternatively, the restraint may be over-molded directly to the spacer.

FIGS. 18A-18D illustrate in detail the components of one embodiment of the tissue modification device. As shown in FIG. 18A, the tissue modification device includes a spacer 1800 and at least one restraint 1801 coupled to the outer edges of the spacer. The spacer includes a distal portion 1800 positioned within the tissue modification region of the device, adjacent to the cutting wires (labeled 1803 in FIGS. 18B-18D), and a proximal portion 1802. In this embodiment, the distal end of the spacer 1800 is fixed to the distal end of the device and the proximal end 1802 is movably coupled to the proximal end of the device via a spring (labeled 1808 in FIGS. 18C and 18D). In some embodiments, the tissue modification region of the device may range from 1 cm to several inches long. The tissue modification region is preferably long enough to reciprocate against and cut through a facet joint, for example. In some embodiments, a longer tissue modification region may have the added benefit of increased fatigue life of the cutting wires due to distributing the cutting load across longer wires. Alternatively, it is also desirable to design the tissue modification region such that it is not so long that the cutting wires will approximate toward one another and adversely affect the effectiveness of the device.

As shown in FIG. 18B, the device further includes cutting wires 1803. As shown, the cutting wires are positioned (at least initially) adjacent to the restraints 1801. In this embodiment, the device may also include cables 1804 toward the distal end of the device and 1805 toward the proximal end of the device. As shown, in this embodiment, cutting wires 1803 and cables 1804 and 1805 are all one continuous cable the runs from the proximal end to the distal end, through the guidewire coupler 1806 at the distal end of the device, and back to the proximal end. In some embodiments, the cutting wire portion of the cable may include blades or other suitable cutting edges. In some embodiments, the cutting edges may be sanded down or otherwise removed from the non-cutting portions of the cable (1804 and 1805). Alternatively, cables 1804 and 1805 may be different cables or different materials coupled to cutting wires 1803. Furthermore, the single continuous cable may not wrap all the way through the distal end of the device. Alternatively, a separate cable may loop through the distal end of the device (rungs 1809 in FIG. 18D) and the distal end may be coupled to the tissue modification region of the device with a separate coupling mechanism. Alternatively there may not be a cable in the distal or proximal ends of the device.

As shown in FIG. 18C, the device may include a proximal end 1807 and a spring 1808. As described above, the spring 1808 may function to movably couple the proximal end of the spacer 1802 to the proximal end of the device 1807 such that the spacer may move with respect to the cutting wires 1803. As shown in FIG. 18D, in some embodiments, the device may further include distal rungs 1809 and distal rungs 1810. These rungs may function to add structure to the device while maintaining thinness and flexibility.

Figure 19A:
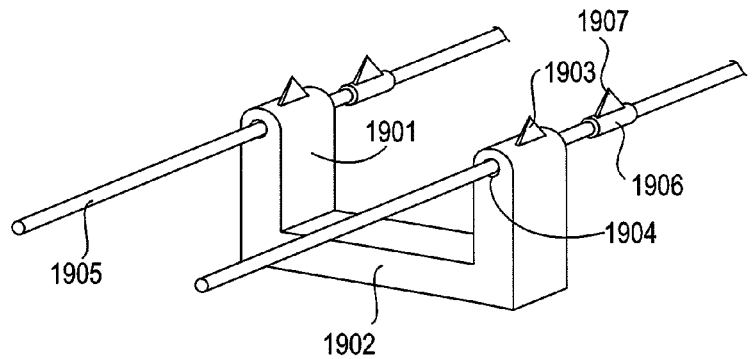
FIGS. 19A-19B illustrate a variation of a rung of the tissue modification device having a U-shaped cross section.
Figure 19B:
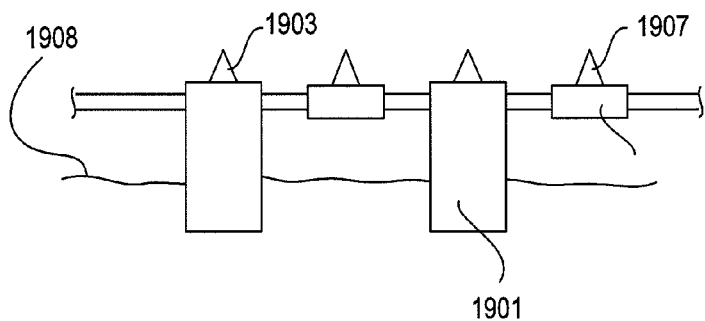

In some embodiments, as shown in FIG. 19A, the spacer may have a "U" shape (e.g. a rounded or a squared off U-shape). The spacer may include two leg portions 1901 and a base portion 1902. The leg portions may be perpendicular to the base portion, or may be configured in any other suitable fashion. The leg portions may be substantially straight, or may have a curved configuration. The spacer may define an opening 1904 through which a cable 1905 or other connector may be threaded. In some embodiments, the spacer may include a cutting edge 1903. The cutting edge may be coupled to the leg portions of the spacer above the opening 1904. As shown in FIG. 19B, the U-shaped spacers may function to allow the legs of the spacers to pass through tissue 1908, such as ligament and bone, as the cutting edges cut through the tissue, such that the base portion of the spacer does not catch on the tissue or otherwise obstruct the cutting of the tissue. As shown, a number of U-shaped spacers may be coupled to a cable to form a modification device. In some embodiments, secondary spacers 1906 may be coupled to the cable between two adjacent U-shaped spacers. The secondary spacers 1906 may include a cutting edge 1907.

Figure 20A:
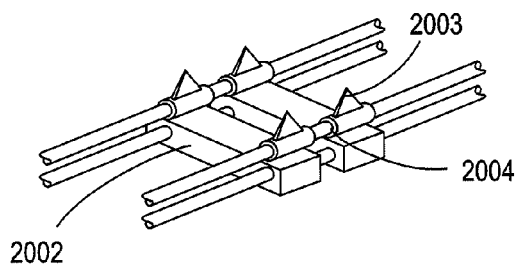
FIGS. 20A-20B illustrate another variation of a rung of the tissue modification device having a U-shaped cross section.
Figure 20B:
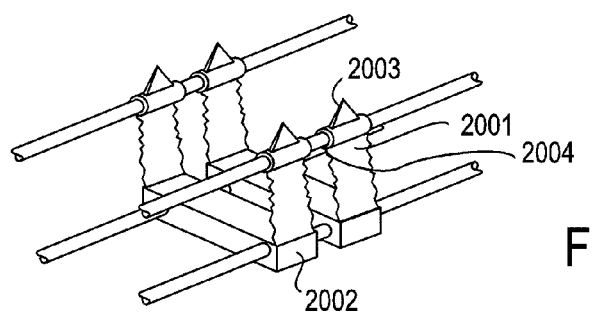

In some embodiments, the leg portions may be flexible. As shown in FIGS. 20A-B, the leg portion 2001 of the U-shaped spacer may be made from an expandable or stretchable material, such that as the cutting edge 2002 cuts through a tissue, the cutting edges and leg portions may extend further into the tissue (FIG. 20B), while the base portion 2002 remains on the surface of the tissue and does not catch on the tissue or otherwise obstruct the cutting of the tissue.

In some embodiments, the device further includes a sheath that covers the cutting edges while the device is being introduced into a patient. Once the device has been introduced, the sheath may be removed. In some embodiments, the sheath further functions to remove the cut tissue.

Figure 21A:
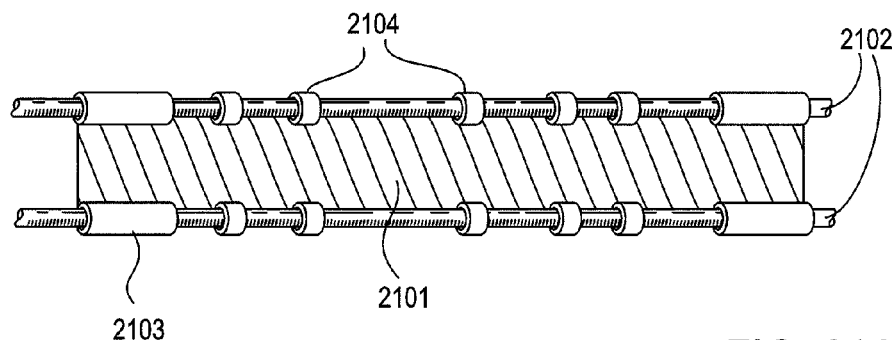
FIGS. 21A-29 illustrate additional variations of the cutting devices and regions of cutting devices described herein.
Figure 21B:
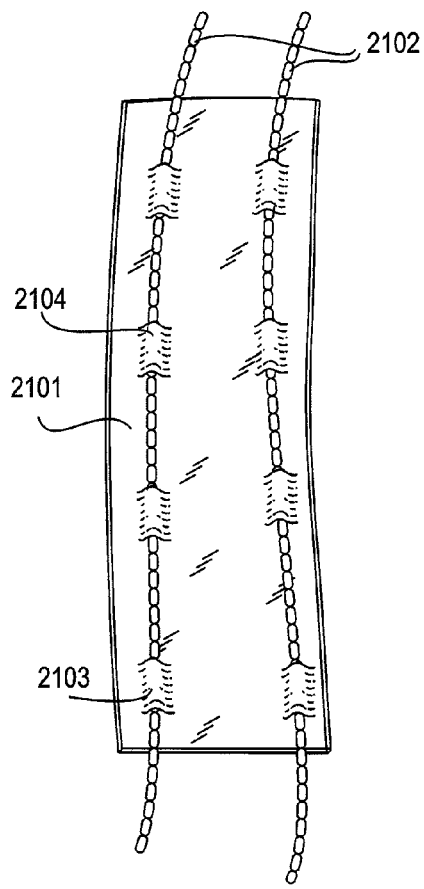
Figure 21C:
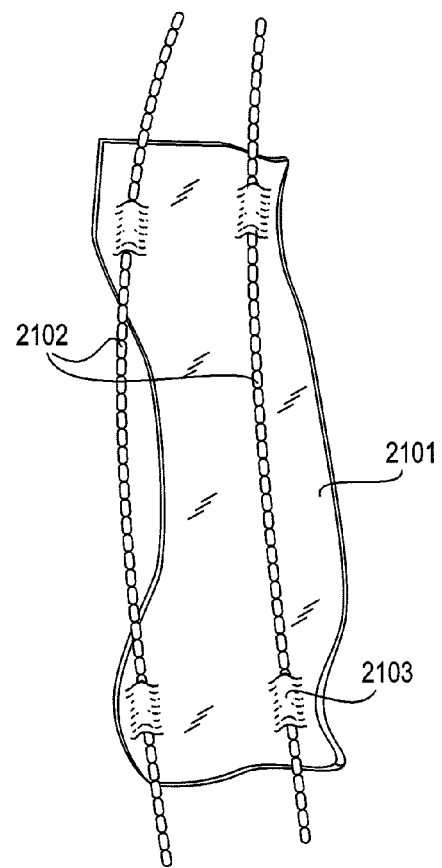

In some embodiments, as shown in FIGS. 21A-21C, a spacer element 2101 may be removably coupled to the cutting wires 2102 of the tissue modification device. The spacer element may be coupled to the cutting wires by a combination of sliding elements 2103 and/or breakaway elements 2104. The spacer may be flexible, rigid, or semi-rigid. Preferably, the spacer is rigid enough in the direction perpendicular to the width of the spacer to prevent the cutting wires from approximating closer to one another than a desired width. For example, a desired width may be 8-15 mm, i.e. the width of an interbody device and or the width or thickness of a facet joint. The spacer 2101 may be flexible in the longitudinal direction and less flexible along its width. In some embodiments, as shown in FIGS. 21B and 21C, the spacer may be made of a silicone material or other suitable polymer. In use, the spacer may initially be coupled to the cutting wires by both sliding elements 2103 toward the ends of the spacer and by breakaway elements 2104 toward the center of the spacer, as shown in FIGS. 21A and 21B. The breakaway elements may be slidably attached or fixed to the cutting wires. The spacer is configured to maintain the distance between the cutting wires while the wires are positioned within the patient and during the initial reciprocations of the tissue modification device against the tissue. As the device is pulled back and forth (i.e. reciprocated) across the tissue, the exposed portions of the cutting wires 2102 will begin to cut through the bone and/or soft tissue. In some embodiments, the device is pulled "up" (toward the back of the patient) and against the tissue while the device is reciprocated across the tissue. Due to this upward pressure, the cutting wires will begin to cut into the tissue and create troughs into the tissue. As the cutting wires cut tissue, they will also cut through the breakaway elements 2104, such that the spacer is released from the breakaway elements, as shown in FIG. 21C. An additional benefit to cutting troughs, as will be described throughout, is that by burying the cutting elements within the troughs created in the tissue the neural and vascular structures (i.e. non-target tissue) will have limited exposure to the cutting wires. Alternatively, the breakaway elements may release the cutting wires independently and are not necessarily cut by the cutting wires. Once the spacer is released by the breakaway elements, the spacer may be permitted to slide along the cutting wires at the sliding elements 2103. This feature is desirable in order to allow the ends of the spacer to slide toward one another along the length of the wires such that the center of the spacer moves away from the cutting wires, as shown in FIG. 21C. This allows the cutting wires to cut deeper into the tissue without the spacer preventing or blocking the wires from cutting all the way through the tissue. Additionally, the spacer may be configured to catch or carry the cut and/or removed tissue in the space created between the spacer and the cutting wires.

Figure 22A:
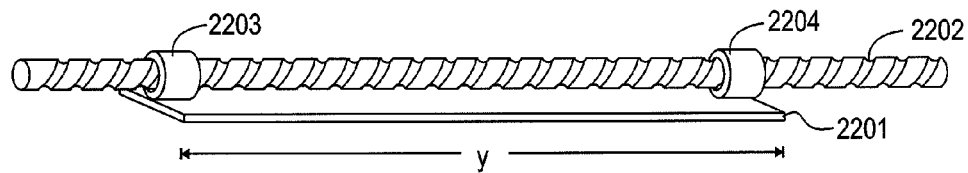
Figure 22B:
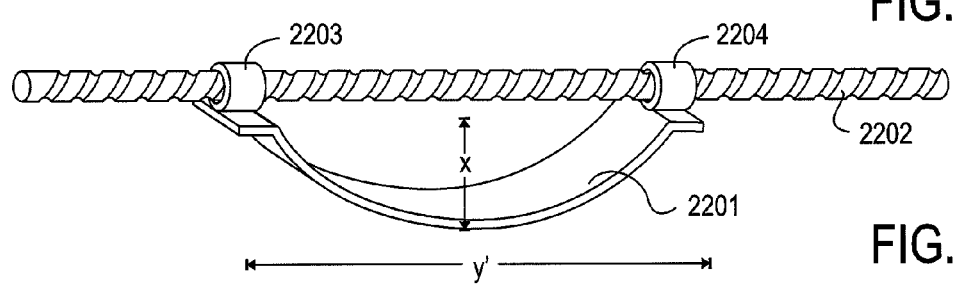

FIGS. 22A-22B illustrate a side view of an alternative variation of a spacer between the cutting wires. As shown, the spacer 2201 is coupled to the cutting wires (only a single wire 2202 is shown) via a sliding coupler 2203 and a fixed coupler 2204. Sliding coupler may be located a distance y from the fixed coupler. Alternatively, both couplers may be slidably connected to the cutting wire 2202. As the cutting wires are reciprocated across the tissue, the cutting wires begin to cut into the tissue creating troughs into the tissue. As the cutting wires enter deeper into the tissue, the spacer rides along the outer surface of the tissue (substantially between and/or below the troughs being cut into the tissue). The spacer must therefore separate from the cutting wires such that the cutting wires can continue to cut deeper troughs and move into the tissue without being restricted by the spacer. The sliding end 2203 of the spacer slides toward the fixed end 2204 of the spacer such that distance Y is reduced to Y' and such that distance X between the center of the spacer and the cutting wire increases as shown in FIG. 22B.

Figure 23A:
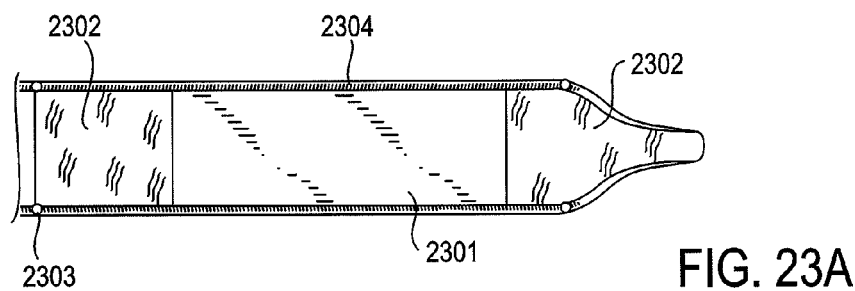
Figure 23B:
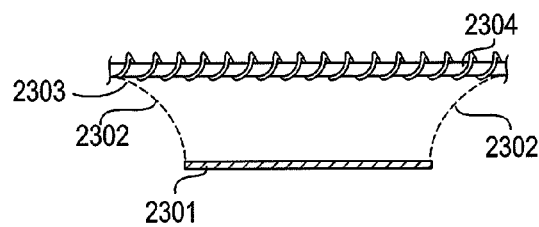
Figure 23C:
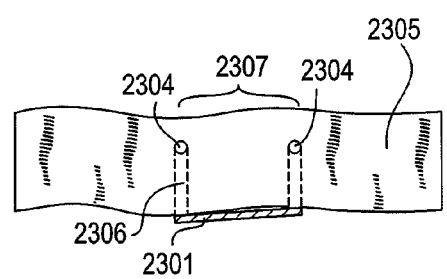

As shown in FIGS. 23A-23C, a rigid (or semi-rigid) spacer 2301 may be coupled to the cutting wires 2304 via at least one flexible portion 2302. The flexible portion 2302 may be fixed to the cutting wire by coupling element 2303. Coupling element 2303 may fix the flexible portion 2302 to the cutting wire 2304, but may alternatively slidably couple the flexible portion to the cutting wires. As described above, the rigid spacer is configured to hold the cutting wires at a desired width. The spacer will hold the wires apart while the device is positioned and while the initial cutting occurs. As shown in cross sectional view and axial view in FIGS. 23B and 23C respectively, as the cutting wires 2304 cut deeper into bone 2305 (or other tissue), the tissue (specifically tissue section 2307) prevents the spacer from entering into troughs 2306 formed by the cutting wires 2304. The spacer therefore "pops" off of and/or away from the cutting wires 2304, thereby stretching flexible portion 2302. As shown in FIG. 23C, the spacer remains exterior to the target tissue as the cutting wires cut deeper into the target tissue. For example, tissue section 2307 may include a facet joint. As the cutting wires are reciprocated and moved up through the tissue, eventually the section 2307 of tissue will be completely cut away from the remainder of the tissue 2305.

Figure 24A:
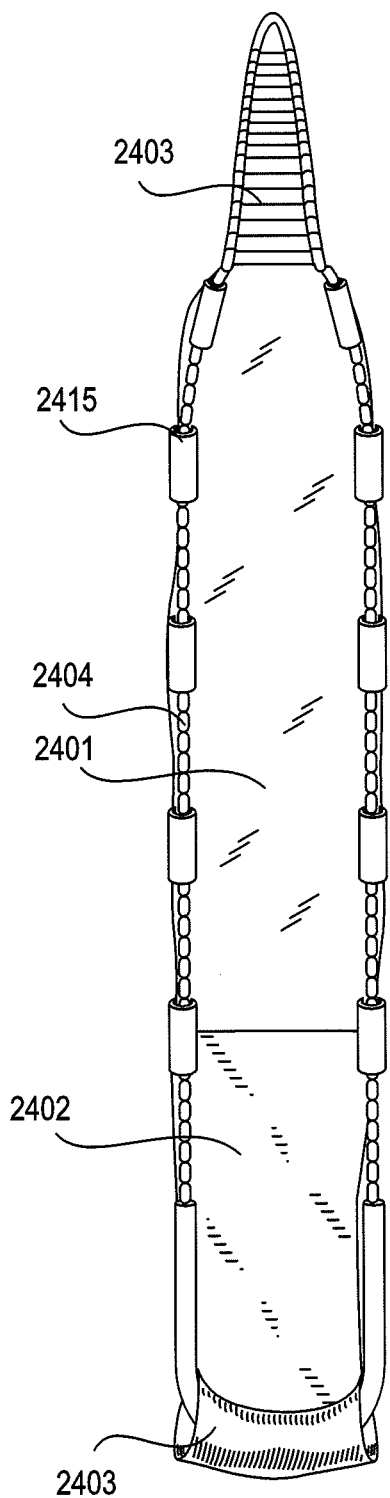
Figure 24B:
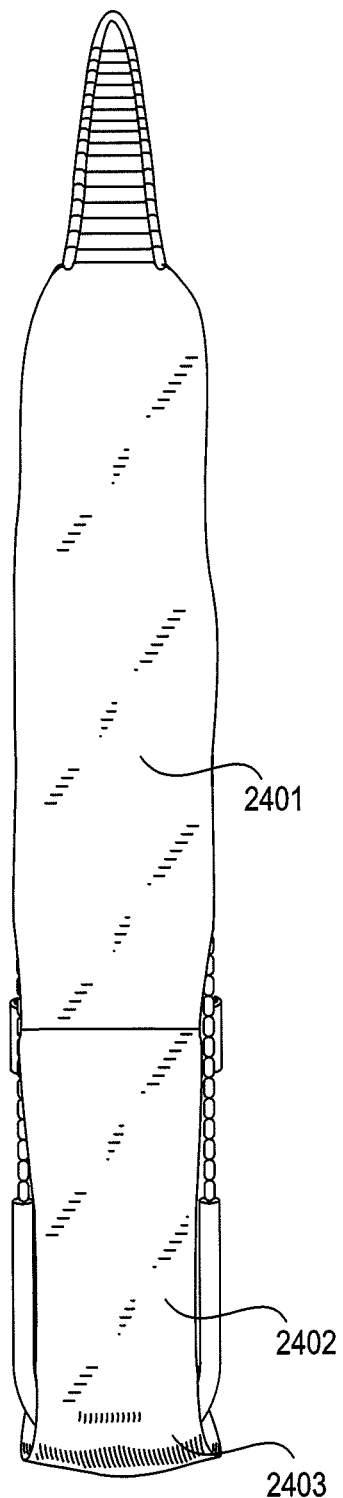

FIG. 24A illustrates a top view of a tissue modification device, and FIG. 24B illustrates a rear view of the same tissue modification device. The device shown may be inserted into a spine and around a facet joint, for example, such that the top portion of the device (FIG. 24A) faces target tissue (e.g. a facet joint) and the bottom portion of the device (FIG. 24B) faces non target tissue (e.g. neural or vascular tissue). As shown in FIGS. 24A and 24B, a rigid (or semi-rigid) spacer 2401 may be coupled to the cutting wires 2404 via at least one flexible portion 2402. As shown, the flexible portion may extend the length of the tissue modification device such that the spacer 2401 may be coupled to the back side of the flexible portion, as shown in FIG. 24B. The flexible portion, in this variation, is fixed to the tissue modification device at positions 2403. As described above, the spacer is configured to hold the cutting wires at a desired width. The spacer will hold the wires apart while the device is positioned and while the initial cutting occurs. In this variation, the spacer 2401 is coupled to the cutting wires 2404 by breakaway elements 2415. As described above, the breakaway elements may be slidably attached or fixed to the cutting wires. As the device is pulled back and forth (i.e., reciprocated) across the tissue, the cutting wires 2404 will begin to cut through bone and/or soft tissue. In some embodiments, the device is pulled "up" (top side of the device toward the back of the patient) and against the tissue while the device is reciprocated across the tissue. Due to this upward pressure, the cutting wires will begin to cut into the tissue and create troughs into the tissue. As the cutting wires cut tissue, they will also cut through the breakaway elements 2415, such that the spacer is released from the breakaway elements.

Figure 25:
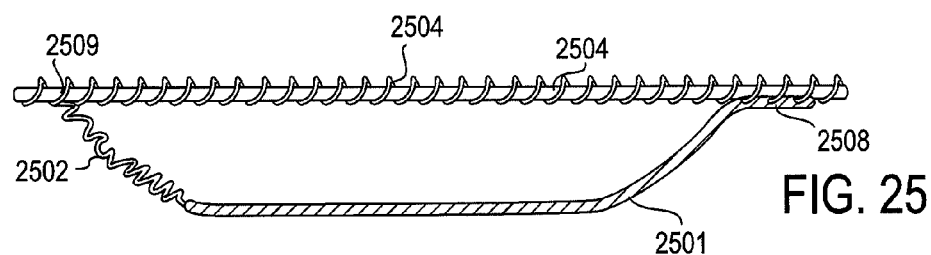

In an alternative variation, as shown in FIG. 25, the spacer 2501 may include only a single flexible portion 2502. In this variation, the spacer may be coupled to the cutting wires 2504 at a first end 2508 while the flexible portion is coupled to the cutting wires 2504 at a second end 2509. As shown, the spacer 2501 is preferably rigid in a first plane (across the width of the device, i.e. into the page) such that it will prevent approximation of the cutting wires. The spacer may be flexible in a second plane (along the length of the device) and/or in a third plane (across the thickness of the device, i.e. up and down with respect to the FIG).

Figure 26A:
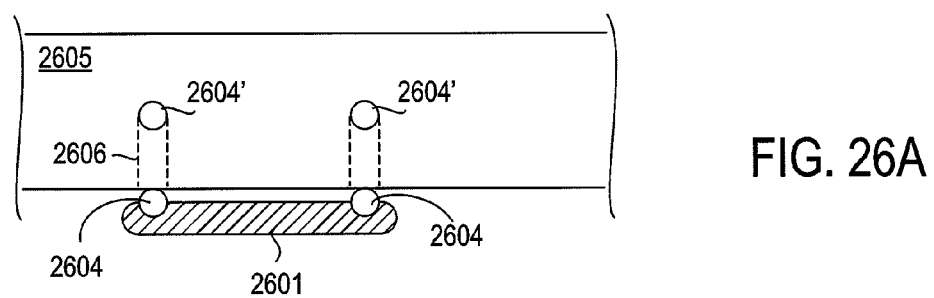
Figure 26B:
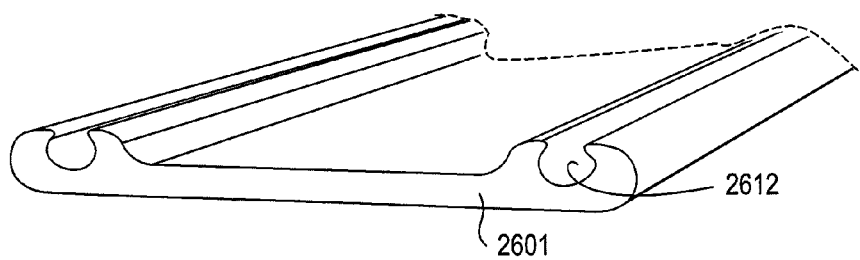
Figure 26C:
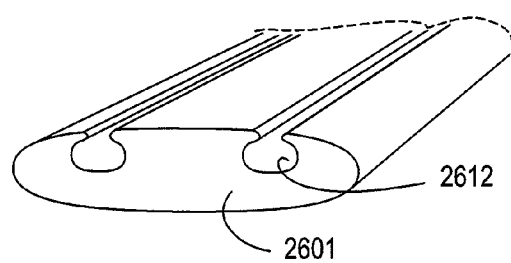

In another alternative embodiment, the rigid or semi-rigid spacer 2601, as shown in FIGS. 26A-26C is removably coupled to the cutting wires 2604. As shown in cross sectional view in FIG. 26A, as the cutting wires 2604 cut deeper into bone 2605 (or other tissue), the tissue 2605 prevents the spacer from entering into troughs 2606 formed by the cutting wires 2604. The spacer therefore "pops" off of and away from the cutting wires 2604' that are within the tissue 2605. As shown in FIG. 26A, the spacer 2601 remains exterior to the target tissue as the cutting wires 2604' cut deeper into the target tissue. In some variations, the cutting wires 2604 may be able to slide within the troughs 2612 of the spacer. In this variation, the spacer may be static (i.e. not reciprocating) while the wires are reciprocated. The material of the spacer may be a molded polymer, or alternatively an extruded polymer. The elastic nature of the material would facilitate both loading and release of the cutting wires.

Figure 27A:
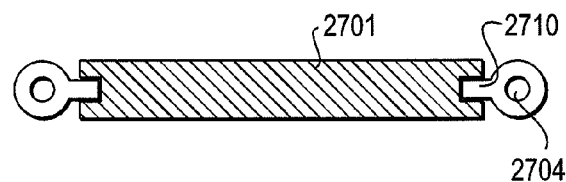

In yet another alternative variation, as shown in cross section in FIG. 27A, rather than "popping" off of the cutting wires 2704, the spacer 2701 is configured to slide off of the cutting wires. In some variations, the spacer may not be removed completely from the tissue modification device, but may be removed from a portion of the cutting wires to allow at least a portion of cutting wires 2704 to cut into and/or through tissue. In some embodiments, the spacer may bunch and fold up along the cutting wires rather than sliding completely away. As shown in FIG. 27A, the spacer may further include coupling elements 2710 that are configured to removably couple the spacer to the cutting wires 2704. Coupling element 2710 may be crimped, welded or coupled to the cutting wire in any suitable fashion. In some variations, the cutting wires may be replaced by non cutting cables and the coupling elements 2710 may include cutting edges (not shown).

Figure 27B:
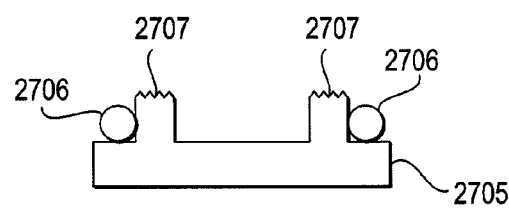

FIG. 27B illustrates (in cross section) an alternative embodiment of a spacer 2705. For example, as shown in FIG. 27B, the spacer may include cutting ridges 2707. These cutting ridges may extend such that they have a height that is greater than the diameter of the cutting wires 2706. The cutting ridges may function to hold the cutting wires a distance apart from one another and prevent the cutting wires 2706 from approximating. The spacer is configured to maintain the distance between the cutting wires while the wires are positioned within the patient and during the initial reciprocations of the tissue modification device against the tissue. As the device is pulled back and forth (i.e. reciprocated) across the tissue, the cutting ridges will begin to cut through the bone and/or soft tissue. In some embodiments, the device is pulled "up" (toward the back of the patient) and against the tissue while the device is reciprocated across the tissue. Due to this upward pressure, the cutting ridges will begin to cut into the tissue and create troughs into the tissue. The cutting ridges may be positioned at discrete locations along the length of the device. Therefore, as the initial troughs are formed, eventually, the cutting wires may fall into the troughs and continue cutting deeper troughs as the spacer moved away from the cutting wires.

In any of the variations described above, the spacer may additionally be configured to function as a shield that functions to prevent non-target tissue such as nerves or arteries from damage while the tissue modification device is used to cut and/or modify tissue within a patient. In some embodiments, the spacer and/or shield may include electrodes and may be configured to detect neural structures as described in conjunction with FIG. 1C. Alternatively or additionally, the spacer and/or shield may be configured to deliver drugs, haemostatic agents, or other suitable agents. In some embodiments, the spacer and/or shield may be tapered. For example, the distal end may be narrower than the proximal end such that the user may pull the device into position. The tapered nature of the spacer ensures that the surgeon can pull the device in as far as is desired before beginning reciprocation, thereby optimally separating the wires before pulling them into the tissue. For example, to perform a pedicle to pedicle Facetectomy, the user may pull the device in until each side of the device is against a pedicle.

In some embodiments, the device may be configured to aid in the releasing of adhesions. For example, the facet capsule or bone may be adherent to dura, neural or vascular elements in the foramen. To facilitate the surgeons' or users' ability to release these potential adhesions and ensure that the facet is free from these vulnerable tissues, one of the following devices described may be helpful.

Figure 28:
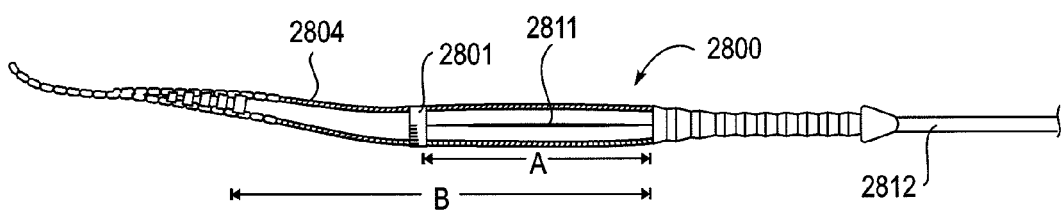

In some embodiments, the spacer is a slider element 2801 as shown in FIG. 28. Slider element 2801 is coupled to cable 2811 which may be coupled to an actuator (not shown) located on the proximal portion 2812 of the device, in some instances, at or near a proximal handle. As the tissue modification device 2800 is inserted into and positioned within a patient, slider is positioned toward the center of the tissue modification portion of the device, e.g. toward the center of the cutting wires 2804. As shown, the slider is positioned a distance A from the distal end of the cutting wires and a distance B from the proximal end of the cutting wires. A user may position the distal portion (distance A) around the target tissue. Slider 2801 may limit the initial stroke length of the reciprocations to substantially the length A. A shorter stroke length may provide greater control and/or less of a propensity for the wires to approximate during reciprocation. Once a user has initiated cutting with the cutting wires 2804 and/or once the cutting wires have formed initial troughs in the target tissue, the slider may be slid proximally to increase the stroke length from length A to a length equal to or less B.

Figure 29:
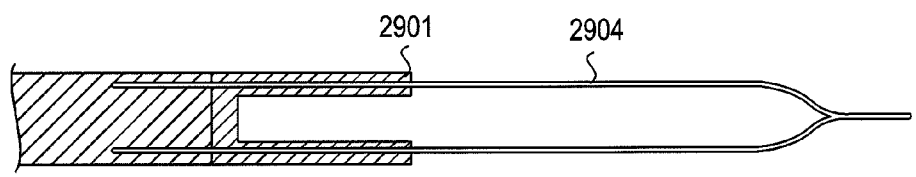

As shown in FIG. 29, in an alternative variation, the slider 2901 may have a pronged configuration. The slider in this configuration is rigid, at least across the width of the device, to prevent the wires 2904 from approximating during reciprocation. The slider may be pronged such that the pronged portions may be inserted into the troughs created by the cutting wires. As described above, the slider may be coupled to an actuator.

FIG. 30A illustrates a cross-section through one variation of a facet-joint modifying device that includes two bone-sawing elements 3002, 3002'. The two saw elements (which may be cables or surfaces including blades) may be separated by a spacer 3005. FIG. 30C shows a top view of one variation of a facet-joint modifying device configured to perform a facetectomy. The distal end of the device is configured to couple with the pull wire, as described above. The tissue-contacting portion of the device may include two parallel cutting surfaces (which may be cables) 3002, 3002' that are separated from each other. These two separate cutting surfaces may allow two cuts to be made through the facet joint simultaneously, permitting removal of a portion of the facet joint. This version of the facet-joint modifying device may also include one or more spacers 3005. Spacers may prevent the cutting surfaces from spreading or contracting towards each other, particularly if the cutting surfaces are cables. In some variations these spacers may be removable or separating, so that as the facet joint modifying device cuts the facet joint, pressure applied as that device is reciprocated against the bone may cause separation, breaking, or removal of the spacer. FIG. 30B illustrates a cross-section through one portion of the device having a breakable (e.g., frangible) spacer 3005.

Tissue Modification Device Having Single Tissue-Modifying Surface

Figure 32:
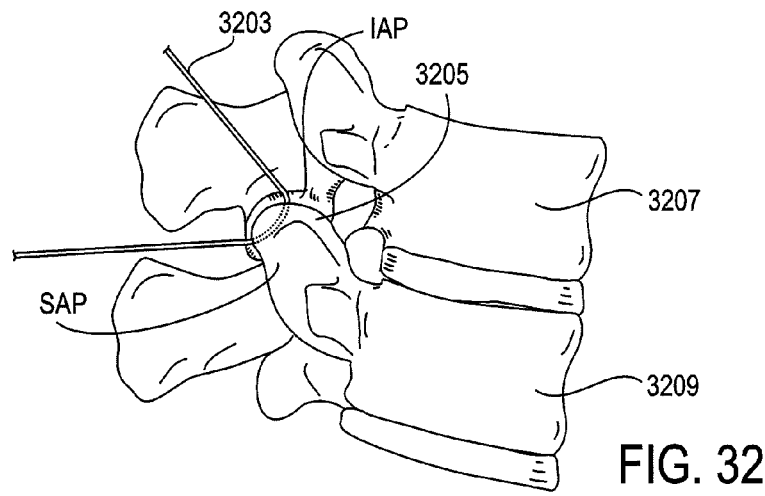
FIG. 32 illustrates a facet joint including the superior and inferior articulating processes.

Other facet joint modifying devices (including those shown in FIGS. 31A-31E) may include a single tissue-modifying surface, and thus does not need a spacer. In one variation of a method for performing a facetectomy, a cannulated probe for guiding a guidewire/pull wire is first inserted in and/or around the joint. FIG. 32A illustrates a facet joint 3205 including the superior articulating process (SAP) and inferior articulating process (IAP) between the lower 3209 and upper 3207 vertebra. A guidewire/pull wire may be threaded through, around, or adjacent to the facet joint as indicated generally by the line 3203. In some variations, the pathway through the facet joint passes over the top of the superior articulating process (SAP). In some variations, the pathway through the facet joint passes under the SAP giving access to the tip of the SAP. Placement of the guidewire around or through the facet joint may be aided by distraction of the spinous process. Thus, in some variations, the spinous process may be distracted before performing the procedure.

Once the probe has been used to position the guidewire, it may be removed. As illustrated above, the probe may include one or a plurality of (concentric) cannula including cannulas having different curvatures so that the guidewire may be directed around the joint and pointed toward the appropriate exit site. The guidewire or pull wire may then be pushed through the cannula and out of the patient. A distal handle may then be attached to the distal end of the guidewire to aid in manipulating the guidewire/pull wire from the distal end.

Next, a treatment device may be pulled into position in or around the joint by coupling the distal end (or end region) of the joint treatment device to the proximal end of the guidewire/pull wire. In some variations the treatment device includes one or more surfaces that are configured to abrade, scratch or otherwise remove bone to perform a facetectomy. For example, FIGS. 31A-31E illustrate variations of a treatment device. In FIG. 31A, the treatment device includes a front and a back articulating surface that can be drawn across the joint surfaces to roughen them and/or remove bone from the joint. In this example, the distal end of the device includes an attachment/connector site for the guidewire. The proximal end also includes an elongate member and may have a proximal handle. In some variations the roughening surface is expandable, so that it may be pulled into the joint in a collapsed or condensed form (protecting non-target tissue), and once in the joint it can be expanded to the treatment form. For example, the device may be inflatable; inflation may expand the device so that the contact surface(s) can push against the joint surface(s). Once in position, the device can be moved bimanually within or around the joint to scrape or otherwise modify the joint to remove bone, by pulling distally and proximally (e.g., back and forth).

FIGS. 31B-31D illustrate alternative cross-sections for the joint treatment devices described. For example, in FIG. 31B, the device is substantially flat, having an upper and lower surface. As mentioned, this device may be inflatable/expandable to increase (or decrease) the spacing between the upper and lower surfaces, or to "stiffen" the implant once it is expanded. FIG. 31C shows a device having an oval cross-section, and FIG. 31D shows a device having a round cross-section. In all of these variations the devices include 'teeth' or protrusions that are configured to remove or modify bone or other tissue. In some variations the devices are configure to abrade, cut, and/or remove cartilage in the joint. In some variations the device is configured to abrade cartilage without substantially cutting or removing bone. In some variations the device surface is configured to abrade cut and/or remove bone from the joint and or remove the joint all together.

The device may be actuated by moving it backwards and forwards (proximally and distally), by bimanual reciprocation. In some variations, such as that shown in FIG. 31E, for example, the device may also or alternatively be articulated by rotating it axially once it is in position in the joint or around the joint.

Expandable Tissue Modification Devices and Methods

Some variations of the tissue modification devices described herein include an elongate, flexible element having a first width and a second width and a tissue modification element coupled to the flexible element. The flexible element may include an expanding mechanism that expands at least a portion of the flexible element from the first width to the second width. Each of these features is described and illustrated in greater detail below.

Figure 33:
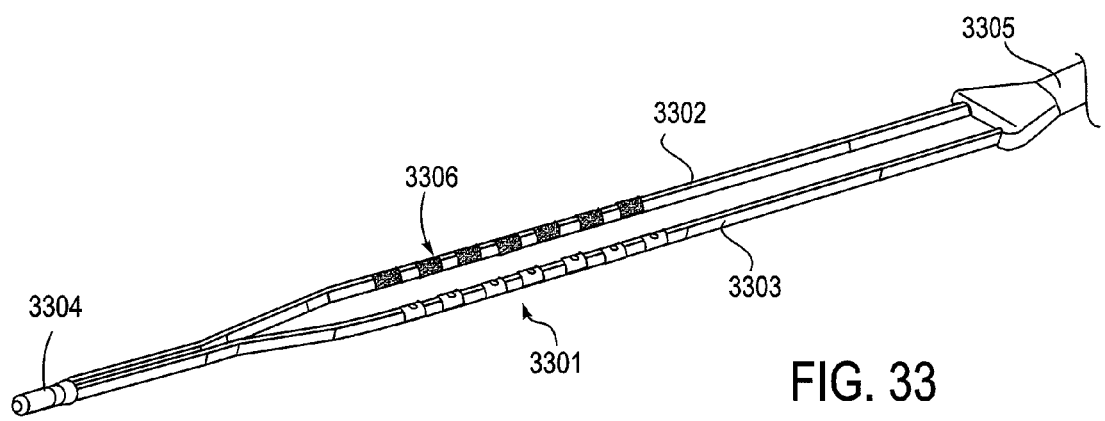
FIGS. 33-35 illustrates multiple variations of a tissue modification device as described.

As shown in FIG. 33, in some embodiments, the tissue modification device includes an elongate, flexible element 3301 having a first width (not shown) and a second width (shown). The flexible element has an axial length, a width (first and second) and a thickness. As shown, the axial length is greater than the width, and the width is greater than the thickness. In some embodiments, the first width may be substantially equal to or less than the thickness and the second width may be greater than the thickness. The first width is generally smaller than the second width. The flexible element is preferably sized and configured such that it may be inserted into a patient in the first width, and then expanded to the second width in order to modify target tissue. For example, the flexible element may be expanded to the second width in order to wrap around a facet joint such that element 3302 is on a first side of a facet joint (such as the superior articular process (SAP)) and element 3303 is on a second side of the facet joint (such as the inferior articular process (IAP)) In some variations, the device will modify or remove a width of target tissue that is substantially equal to or greater than the second width of the flexible element. In one specific example, the first width may be 2-15 mm such that the device may fit within an interlaminar window of a patient's spine. The second width may be 5-20 mm such that the device may modify a width of tissue that is 5-20 mm wide such as the facet joint of a patient's spine. In some variations, the second width of the device may range from 8 to 15 mm such that the user may then insert an inter body device, such as a cage, through the opening created to the space between adjacent vertebral bodies. The flexible element may be adjustable to a plurality of second widths. For example, the flexible element may be inserted into a patient at a first width and then advanced such that it is adjacent to a target tissue, around a facet joint for example. The flexible element may then be expanded until it contacts an adjacent pedicle or other suitable anatomy and can no longer expand.

The flexible element 3301 may include two flexible elongate cables 3302 and 3303 that are expandable from the first width to the second width. The wires may be configured such that for the first width of the flexible element, the wires are adjacent to one another and/or substantially touching along their length. The wires may then be separated from one another, as shown in FIG. 33, such that the flexible element has a second width. The cables may extend substantially adjacent to each other from the proximal end of the device to the distal end of the device. At least a portion of the cable is flexible. Any appropriate cable may be used, including metal or polymeric cables. Cables may be single-filament or formed of multiple filaments. The portion of the cable towards the distal end of the device, as shown in this example, may be hinged or otherwise coupled to a coupling element 3304. Coupling element 3304 may be configured to receive an end of a guidewire or pull wire, such that flexible element may be pulled and/or positioned by the pull wire.

In FIG. 33, the flexible element 3301 of the device is joined to the proximal end of the device 3305, which may be less flexible, and may include a handle or an attachment region for a handle. This interface between the flexible cables and the proximal end and/or handle may be a joint or hinge, or any other suitable coupling mechanism. The proximal joint near the proximal end may be a ball joint, in some embodiments, which allows the rotation of the handle and/or proximal portion of the device with respect to the tissue modification region and/or flexible element of the device. Thus, the proximal handle may be rotated along the long axis of the tissue modification device, but will not substantially torque the tissue modification region of the device. The variation shown in FIG. 33 may also include a proximal connecting region near the proximal end 3305 of the device to which a handle is attached. This connecting region may be relatively stiff (or inflexible), or it may also be flexible.

Figure 34:
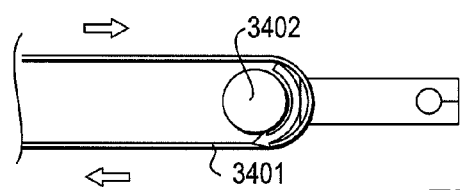

In some embodiments, as described below, the flexible element may comprise a balloon or other suitable flexible element. In some embodiments, as shown in FIG. 34, the flexible element may comprise a loop of cable, rather than two separate cables. Cable loop 3401 may be expandable from the first width to the second width. The cable loop may be configured such that for the first width of the flexible element, two side portions of the loop are adjacent to one another and/or substantially touching along their length. The two side portions of the loop may then be separated from one another, as shown in FIG. 34, such that the flexible element has a second width. The device may further include a pulley 3402 or other suitable gear or wheel, as shown in FIG. 34, about which the cable loop may be wound. The pulley may function to expand the cable loop from the first width to the second width, and or may function to aid in the reciprocation of the cable loop for cutting tissue as described below.

The tissue modification device includes a tissue modification element coupled to the flexible element. In a first embodiment, the flexible element includes at least one wire that is configured to cut tissue or otherwise modify tissue. The wire may be textured or coated such that it is adapted to cut tissue. As shown in FIG. 33, the device further includes at least one cutting edge 3306 coupled to at least a portion of the flexible element 3301. In some embodiments, the cutting edge is crimped onto the cable. The tissue modification device may include cutting edges directly coupled to a cable, it may include ferrules or beads threaded onto the cables onto which a cutting edge is fixed or integrated, or the device may include any other suitable cutting edges coupled to the flexible element in any suitable fashion. The flexible element may include cutting elements such as beads, blades, wires, or other suitable cutting elements. As shown in FIG. 33, a portion of the device may include cutting cables, while a portion of the device includes rungs threaded onto cables (with or without cutting edges on the rungs). The tissue modification device may modify or cut tissue by moving the modification elements against the target tissue. In some variations, the device is reciprocated against the target tissue. In an alternative embodiment, a first cable of the flexible element is moved against the target tissue in a first direction, and a second cable is moved against the target tissue in a second direction, and then each cable is reciprocated against the target tissue. Alternatively, in the case of the flexible element comprising a loop of cable, the loop may rotate or be driven against the target tissue, as shown in FIG. 34.

Figure 35:
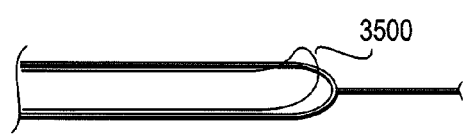

In an alternative embodiment, the tissue modification element may modify tissue using an energy such as heat or radio frequency energy. The energy may function to desiccate and/or shrink the tissue. Alternatively, the energy may function to cut the tissue. As shown in FIG. 35, the flexible element may further include a cutting loop 3500 that functions to cut, desiccate, and/or shrink the target tissue. In some embodiments, the flexible element is coupled to a heating element or other energy source.

Figure 36:
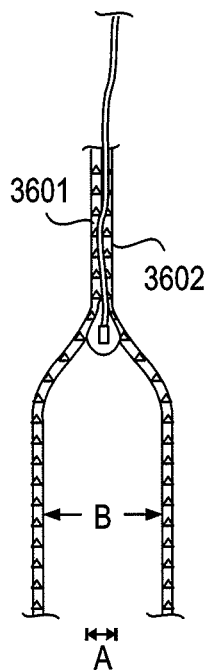
FIG. 36 illustrates one variation of an expanding mechanism as described.

In some embodiments, the tissue modification device includes an expanding mechanism that expands at least a portion of the flexible element from the first width to the second width. In a first embodiment, as shown in FIG. 36, the flexible element comprises two wires 3601 and 3602 expandable from a first width (A) to a second width (B). In some embodiments, the expanding mechanism further functions to hold the flexible elements in position, i.e. hold them a distance apart (the second width) and prevent them from approximating, particularly while modifying tissue with the device.

Figure 37:
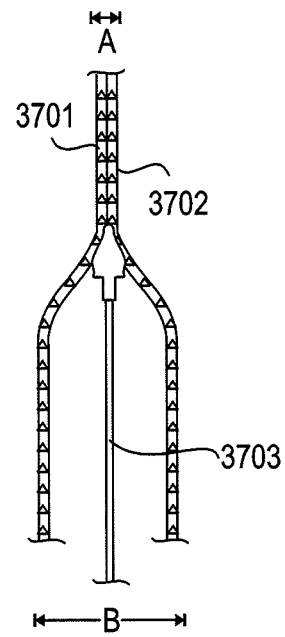
FIGS. 37-41D illustrate other variations of expanding mechanisms as described.

In a first variation, as shown in FIG. 36, the expanding mechanism 3603 is coupled between the two wires 3601 and 3602 and separates the wires from a first width to a second width as the expanding mechanism is moved along the length of the wires. The expanding mechanism may be triangular shaped or otherwise configured to function in a manner similar to a zipper or ZIP-LOCK bag sliding mechanism. Alternatively, as shown in FIG. 37, the expanding element may be an expander rod 3703. The rod may be inserted between the two wires or cables once the wires are in place (i.e. inserted into a patient and/or adjacent to target tissue), and may be sized and configured to expand the flexible element from a first width (A) to a second width (B).

Figure 38A:
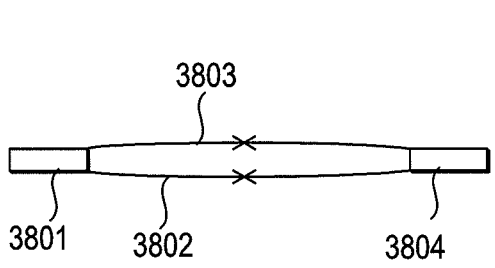
Figure 38B:
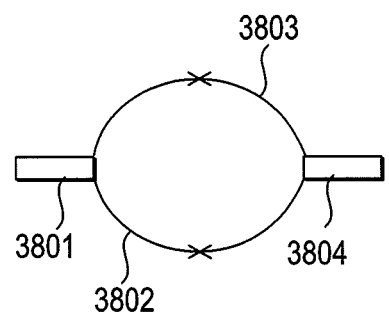

In an alternative embodiment, as shown in FIG. 38, the expanding mechanism comprises a first element 3801 coupled to two wires 3802 and 3803 at a first location and a second element 3804 coupled to the two wires at a second, distal location. The device may be inserted into a patient while the wires are a first width apart, and then by moving the first element 3801 toward the second element 3804, as shown in FIG. 38, the wires expand from a first width to a second width.

Figure 39:
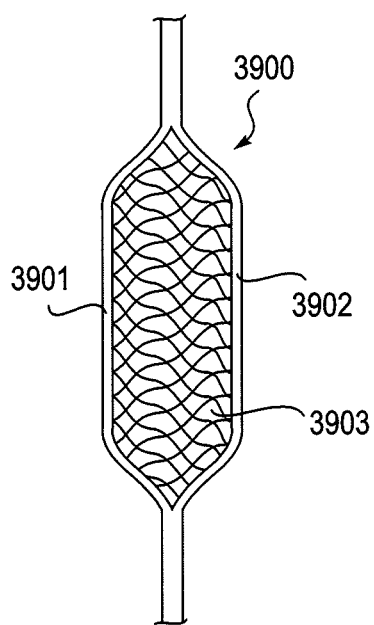
Figure 40:
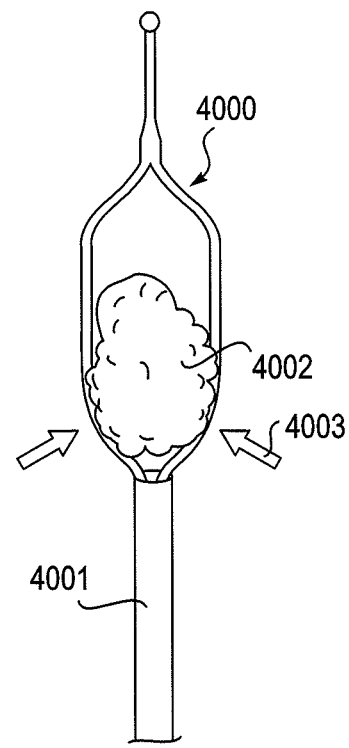

As shown in FIGS. 39 and 40, the expanding mechanism may comprise a frame 3900, expandable from a first width (not shown) to a second width. The frame may be a shape memory material such as Nitinol or any other shape memory, shape changing, or super elastic material. The frame may comprise at least two frame portions (such as wires 3901 and 3902) that are expandable from a first width to a second width. In a first embodiment, as shown in FIG. 39, the frame may further include a mesh 3903 or other material coupled to the frame between the frame portions. The mesh may function to capture and/or remove cut or modified target tissue, such as a facet joint. In some embodiments, the frame may not completely encircle the mesh material, for example, the frame may comprise a distal end and a proximal end, each with an expandable fork structure.

As shown in FIG. 40, the frame may further include a sleeve 4001 coupled to the frame 4000. The sleeve may have a width substantially equal to the first width of the flexible element, such that the frame may be inserted into the sleeve and held at a first width. The sleeve may then be pulled back (shown in FIG. 40 in the pulled back position) to allow the frame to separate. When removing the device after modifying tissue, the frame in some embodiments, may be configured to grab the modified target tissue 4002 as the frame retracts (shown by arrows 4003) and pull the tissue back with the frame into the sleeve 4001 for easy removal of the tissue.

Figure 41A:
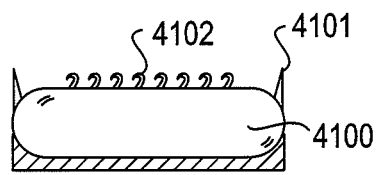
Figure 41B:
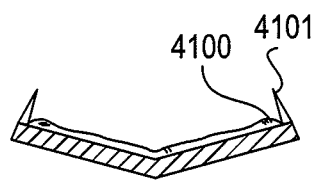

As shown in FIGS. 41A and 41B, in some embodiments, the expanding mechanism is a balloon 4100. The device in this configuration may have cutting blades 4101 coupled to the side portions of the balloon such that the blades may cut a width of tissue substantially equal to the width of the balloon in its inflated or expanded configuration. In this embodiment, the balloon may further include hook 4102 configured to capture soft tissue, such as ligament, for example.

Figure 41C:
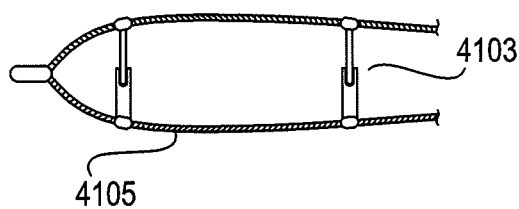
Figure 41D:
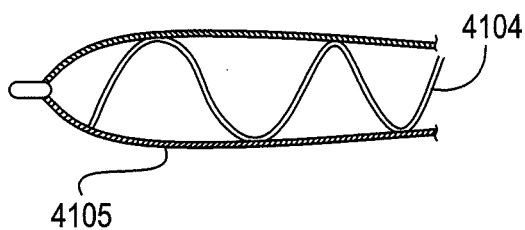

As shown in FIGS. 41C and 41D, the expanding mechanism may be actuator 4103 (FIG. 41B) or actuator 4104 (FIG. 41C). In a first variation, as shown in FIG. 41C, the actuator 4103 is a spring or piston that expands and contracts to move the flexible element 4105 from a first width to a second width (shown). In a second variation, as shown in FIG. 41D, the actuator is wire 4104 made from a shape memory material such as Nitinol or any other shape memory, shape changing, or super elastic material. The wire may be coupled to the flexible element 4105 as shown and is expandable such that it moves the flexible element from a first width to a second width (shown).

Figure 42:
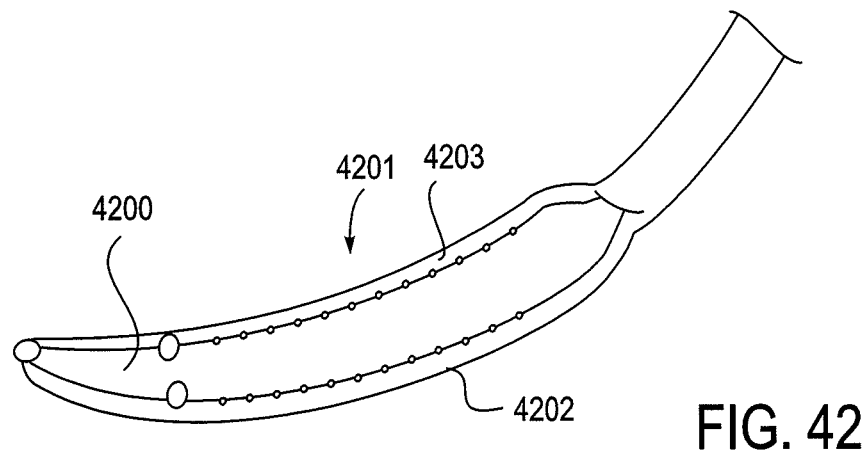
FIG. 42 illustrates one variation of a tissue modification device having a shield as described.

As shown in FIG. 42, the device may include a shield 4200 coupled to the flexible element. The shield may be coupled to the flexible element 4201 such that while the flexible element is adjacent to the target tissue, the shield protects the adjacent non-target tissue, such as neural tissue, and/or may collect the tissue cut and/or modified by the device. In some embodiments, the flexible element functions to slide distally and proximally within or over a substantially stationary shield. In some embodiments, the shield may function to contact and/or engage with and remove tissue (for example, a facet joint) cut and/or modified by the device. In some embodiments, as shown in FIG. 42, the flexible element comprises two wires 4202 and 4203 coupled to a shield and held a distance apart from one another. The shield is coupled adjacent to the bottom surface of the flexible element and is sized and configured to maintain the width of the flexible element by preventing the cables from approximating toward one another while modifying tissue.

In some embodiments, the device may include a tracking element. For example, a tracking element may be disposed in the distal end of the device, such that the tip of the device may be tracked as it is inserted into a patient and/or moved within the patient. Alternatively, the device may include multiple tracking elements disposed along the length of the device, or multiple tracking elements disposed along a portion of the length of the device (for example along the cutting region of the device). In some embodiments, the tracking element is a material that is detectable by an imaging system. Some examples of suitable tracking elements include echogenic materials or substances (i.e. configured to form an echogenic surface) detectable by an ultrasound system, and radio-opaque materials detectable by a radiograph system, such as a fluoroscope. Alternatively, the tracking element may be configured to be detectable by an MRI or Infrared system. In some embodiments the tracking element is preferably a coil configured to be detected by an electromagnetic tracking or navigation system. For example, the devices described herein may incorporate a tracking system such as the AXIEM™ Electromagnetic Tracking Technology, e.g., the StealthStation® AXIEM™ (Medtronic Navigation, Louisville, Colo. USA). In some embodiments, the device is configured to generate an electromagnetic field around a patient's target anatomy that can be tracked to triangulate the positioning of devices having tracking elements.

As mentioned above, any of the device described herein may include a guidewire coupler. A guidewire coupler is configured to attach to a guidewire (e.g., one end of a guidewire) so that the device can be manipulated, at least in part, by pulling on the guidewire after the guidewire has been secured to the device. For example, in some variations a guidewire may be inserted into the body from a first location outside of the body, then passed around the target tissue (e.g., around a spinal foramen) and out of the body from a second position. The distal end of the guidewire may then be coupled to the tissue modification device (such as the one shown in FIG. 33) and pulled through the body until the tissue modifying region of the device, e.g., the portion of the device including tissue modification elements 3306, is positioned opposite the target tissue. In some variations the guidewire used includes a tip region that is enlarged and may engage the guidewire coupler. For example, the guidewire may have a proximal end with a flange or ball. This enlarged region may be configured to fit into an opening on the guidewire coupler so that the guidewire can be pulled distally from outside of the patient. In some variations the distal end of the device may be completely withdrawn, so that it can be grasped and manipulated. In other variations, the distal end of the tissue-modification device remains coupled to the guidewire, and the guidewire may be grasped to manipulate the distal end of the tissue-modification device. A handle may be attached to the guidewire. As mentioned, in operation, the device is urged against the target tissue and may be moved in the proximal/distal direction to modify (e.g., cut) the target tissue. For example, both the proximal and distal ends of the tissue-modification device may be pulled to urge the device against the target tissue, and may each be alternately pulled to a greater degree than the other handle to slide the device over the target tissue, allowing the cutting edges to cut and modify the target tissue.

For example, a guidewire coupler may include an opening and/or channel to receive an enlarged or necked region at the proximal end of the guidewire. This configuration may be similar to the "trailer hitch" configuration described in many of the references previously incorporated by reference.

The methods for modifying tissue described herein typically include one or more of the following steps: inserting an elongate, flexible element having a first width; advancing the flexible element until a portion of the flexible element is adjacent to a target tissue; expanding at least the portion the flexible element adjacent to the target tissue to a second width; and modifying the target tissue with the flexible element. A method for modifying tissue may include one or more of these steps in any combination. Each of these steps is described and illustrated in greater detail below.

The inserting functions to bring the device into position. The inserting step may further include inserting the device into a patient, and more specifically into the spine of a patient, for example. In some variations, the device may be inserted through an interlaminar window of a patient's spine. In this variation, the flexible element is preferably configured in the first width. The first width may be equal to or smaller than the space defined by two adjacent amina (i.e. the interlaminar window). Once inserted, the device may be advanced into position. The device may be moved until it is adjacent to the target tissue. In some embodiments, the advancing step further includes the steps of passing a guidewire at least partially around the target tissue and pulling the device around the target tissue using the guidewire, such that the flexible elements and/or cutting element are adjacent to the target tissue. In some embodiments, the guidewire is coupled to the guidewire coupler at the distal portion of the device. The inserting and advancing steps may be performed while the flexible element is configured in the first width. This allows the device to be smaller and more maneuverable such that it may fit through and around tight anatomical spaces and locations.

Once the device is positioned correctly within the patient, it may be desirable to expand the flexible element from the first width to the second width. The expanded width (second width) is wider than the first width, and allows the cutting elements coupled to the flexible element to modify a wider and/or larger portion or area of target tissue. In some embodiments, the second width may be substantially equal to (or slightly smaller than) the width of a facet joint, the width of the neural foramen of a patient's spine, and/or the width of an interbody fusion device. In some embodiments, the second width may be substantially equal to (or slightly smaller than)

the distance from a first pedicle to an adjacent pedicle. Once the device is expanded, the wider device may be used to modify target tissue.

In some embodiments, the modifying step further includes moving the flexible element across the target tissue. The flexible element may be moved through or over the target tissue. The flexible element may also be reciprocated or moved back and forth across the target tissue in order to modify an area of target tissue. The modification elements may be reciprocated between a distal position and a proximal position. The device may be reciprocated by applying tension to both the proximal end and the distal end of the device to drive the flexible element and/or tissue modification elements against the target tissue.

Figure 43:
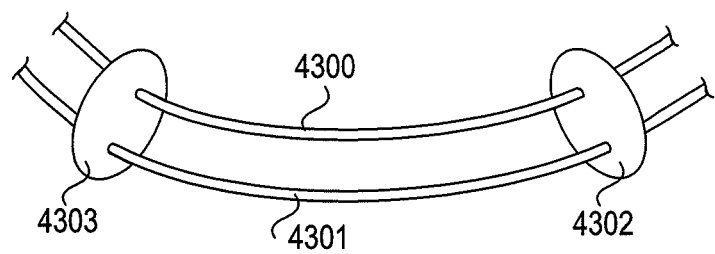
FIG. 43 illustrates another variation of a device and method for modifying tissue as described.

In some embodiments, modifying target tissue may include cutting a width of tissue, such as a facet joint, having a width substantially equal to the second width of the flexible element. As shown in FIG. 43, methods for modifying tissue described may alternatively include one or more of the following steps: inserting a first elongate, flexible element 4300 into the patient at a first location; advancing the first flexible element until a portion of the flexible element is adjacent to a target tissue; inserting a second elongate, flexible element 4301 into the patient at the first location, a distance from the first flexible element; and modifying the target tissue with the flexible elements. A method for modifying tissue may include one or more of these steps in any combination. Each of these steps is described and illustrated in greater detail below.

In some embodiments, the inserting a second flexible element step further includes inserting a second flexible element a distance from the first flexible element, wherein the distance is substantially equal to the width of the facet joint. Alternatively, the inserting a second flexible element step may further include inserting a second flexible element a distance from the first flexible element, wherein the distance is substantially equal to the width of an interbody fusion device. Once inserted, the two flexible elements may be coupled to a distal handle 4302 and/or a proximal handle 4303. The method may further include the steps of coupling the distal end of the first flexible element to a distal handle and then coupling the distal end of the second flexible element to the distal handle.

These steps have the benefit in that the single flexible element may be inserted and easily maneuvered independently through tight anatomical sites and locations. By then inserting a second flexible element (which is also easily maneuvered independently) at an angle to or a distance from the first flexible element such that the tissue modification portions of the flexible elements are adjacent to one another and a distance apart (e.g. a distance substantially equal to the width of the facet joint or the width of an interbody fusion device) and may modify a portion of tissue substantially equal to that distance. In some embodiments, the two flexible elements function to cut a strip of target tissue having a width substantially equal to the distance between the flexible elements.

Delivery Devices and Methods

Figure 44:
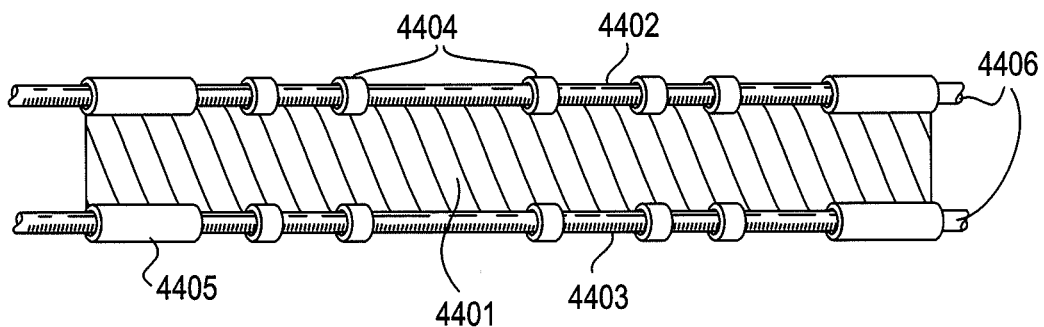
FIG. 44 illustrates a delivery device as described herein.

FIG. 44 illustrates an embodiment of a delivery device for delivering a tissue modification device for removing tissue from a patient. In some embodiments, the device includes a ribbon shaped flexible elongate body 4401 having a width defined by a first edge 4402 and a second edge 4403. In some embodiments, the first and second edges are substantially parallel. The device may also include a first channel disposed along a portion of the length of the elongate body, positioned toward the first edge of the elongate body, and a second channel disposed along a portion of the length of the elongate body, positioned toward the second edge of the elongate body.

As shown, the channels may be made up of elements 4404 and 4405. Alternatively, the channels made comprise a single tubular element (not shown). The channel is sized and configured to receive two elongate cutting members 4406. In some embodiments, the device may also include a guidewire coupler (not shown) at the distal end region of the elongate body 4401.

Also described herein are methods for delivering tissue modification devices for removing tissue from a patient. In some embodiments, the methods include the steps of inserting an elongate, flexible shield 4401 into the patient at a first location; advancing the shield until a portion of the shield is adjacent to a target tissue; inserting a first elongate, flexible cutting element 4406 through the shield until a portion of the first cutting element is adjacent to a target tissue; inserting a second elongate, flexible cutting element 4406 through the shield, a distance from the first cutting element and substantially parallel to the first cutting element, until a portion of the second cutting element is adjacent to a target tissue; and modifying the tissue with the flexible elements.

In some embodiments, the methods include the steps of inserting a first elongate, flexible cutting element 4406 until a portion of the first cutting element is adjacent to a target tissue; advancing an elongate, flexible shield 4401 into the patient, wherein a portion of the shield is advanced over the first elongate, flexible cutting element; inserting a second elongate, flexible cutting element 4406 through the shield, a distance from the first cutting element and substantially parallel to the first cutting element, until a portion of the second cutting element is adjacent to a target tissue; and modifying the tissue with the flexible elements. In some embodiments, the methods further include the step of removing the shield 4401 from the patient while leaving the cutting elements in position within the patient.

Various embodiments of tissue modification devices and systems, as well as methods for making and using tissue modification devices and systems, are provided herein. In general, a flexible tissue-modification device as described herein is configured to remove tissue from a patient. In particular, these tissue-modification devices may be configured to perform tissue removal such as a Facetectomy. These devices typically include a flexible elongate body that extends proximally to distally (proximal/distal), and is configured to be inserted into a patient so that it extends around the target tissue (such as a facet joint of the spine), so that it can be pulled against the target tissue by applying tension to either end of the device. Thus, the device may be extended into or through a spinal foramen, and/or around a spinal facet joint.

Although much of the following description and accompanying figures generally focuses on surgical procedures in spine, in alternative embodiments, devices, systems and methods of the present invention may be used in any of a number of other anatomical locations in a patient's body. For example, in some embodiments, the flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. Thus, various embodiments described herein may be used to modify any of a number of different tissues, in any of a number of anatomical locations in the body, to treat any of a number of different conditions.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A bimanually controlled tissue modification device having a tissue modification region for cutting tissue in a patient, the tissue modification region comprising:
   a pair of flexible elongate cutting members extending along the length of the tissue modification region, wherein each elongate cutting member has a thickness and each elongate cutting member is configured to cut a discrete trough into tissue to a depth that is greater than the thickness of the cutting member,
   wherein at least one cutting member comprises a cutting wire.

2. The device of claim 1, further comprising a guidewire coupler distal to the tissue modification region of the device.

3. The device of claim 2, wherein the guidewire coupler is configured to be coupled to a guidewire, and wherein the tissue modification region is configured to be actuated by a proximal handle and a guidewire.

4. The device of claim 1, wherein the tissue modification region is configured to be actuated by a proximal handle and a distal handle.

5. The device of claim 2, wherein the guidewire coupler is configured such that the device is removably attachable to a proximal end region of a guidewire such that the tissue modification region can be pulled into position by pulling on the guidewire while the proximal end region of the guidewire is held stationary by the guidewire coupler with respect to the device.

6. The device of claim 1, wherein at least one cutting member comprises an elongate wire having a helical cutting edge along the length of the wire.

7. The device of claim 1, further comprising a spacer coupled to the elongate cutting members of the tissue modification region, wherein the spacer is sized and configured to temporarily hold the cutting members a distance from one another.

8. The device of claim 7, wherein the spacer comprises an elongate, flexible, ribbon-shaped substrate.

9. The device of claim 8, wherein the spacer further comprises a restraint located towards the outer edge region of the spacer and configured to temporarily secure a cutting member to the outer edge region of the spacer.

10. An elongate, bimanually controlled tissue modification device for cutting tissue in a patient, the device comprising:
    a pair of flexible, elongate cutting members extending along an elongate length of the device; and
    a spacer, wherein the spacer is sized and configured to operate in one of two modes:
       a first mode, wherein the spacer is coupled to the cutting members such that it holds a portion of each of the two cutting members a distance from one another, and
       a second mode, wherein at least a portion of the spacer is moved away from a cutting member to allow the cutting members to cut further into tissue.

11. The device of claim 10, wherein the elongate cutting members are substantially parallel to one another.

12. The device of claim 10, wherein the spacer in the second mode is positioned out of the plane of the cutting members.

13. The device of claim 10, further comprising a guidewire coupler at the distal end region of the tissue modification device.

14. The device of claim 10, wherein the spacer in the second mode is positioned such that each of the cutting members can cut a depth into tissue that is greater than the thickness of the cutting members.

15. The device of claim 10, wherein the spacer further comprises a restraint configured to couple the spacer to a cutting member while the spacer is in the first mode.

16. The device of claim 10, further comprising a spring, wherein the spring is configured to expand as the spacer transitions from the first mode to the second mode.

17. The device of claim 10, wherein the cutting members are sized and configured to cut a first depth into the tissue while the spacer is in the first mode and to cut a second, greater depth into the tissue while the spacer is in the second mode.

18. The device of claim 10, wherein the cutting members are configured to be actuated by a proximal handle and a distal handle.

19. A method of modifying tissue, the method comprising:
    passing an elongate, flexible tissue-modification device at least partially around a target tissue,
    moving a tissue-modification region of the device against the target tissue by pulling the tissue-modification device from at least one end of the device; and
    cutting two discrete elongate troughs into the tissue with a pair of flexible elongate cutting members extending along the elongate length of the tissue modification region, wherein the elongate cutting members have a thickness and each of the elongate troughs are cut to a depth that is greater than the thickness of the cutting members.

* * * * *